(12) United States Patent
Stuebiger et al.

(10) Patent No.: US 11,684,733 B2
(45) Date of Patent: Jun. 27, 2023

(54) ELECTRICALLY STIMULATED RESPIRATORY ASSISTANCE COMPONENTS

(71) Applicant: ResMed Pty Ltd, Bella Vista (AU)

(72) Inventors: Kai Stuebiger, Sydney (AU); Justin John Formica, Sydney (AU); Aaron Samuel Davidson, Sydney (AU); Gerard Michael Rummery, Sydney (AU); Clancy John Dennis, Sydney (AU); Liam Holley, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 599 days.

(21) Appl. No.: 16/819,137

(22) Filed: Mar. 15, 2020

(65) Prior Publication Data
US 2020/0215277 A1    Jul. 9, 2020

Related U.S. Application Data

(63) Continuation of application No. 15/590,415, filed on May 9, 2017, now Pat. No. 10,806,875, which is a
(Continued)

(51) Int. Cl.
*A61M 16/06* (2006.01)
*A61M 16/00* (2006.01)
(Continued)

(52) U.S. Cl.
CPC ....... *A61M 16/0003* (2014.02); *A47C 31/123* (2013.01); *A61M 16/0057* (2013.01);
(Continued)

(58) Field of Classification Search
CPC ..... A47C 31/123; A61B 1/0058; A61B 1/018; A61B 17/00234; A61B 17/3423;
(Continued)

(56) References Cited

U.S. PATENT DOCUMENTS

| 4,944,310 A | 7/1990 | Sullivan |
| 5,485,850 A | 1/1996 | Dietz |

(Continued)

FOREIGN PATENT DOCUMENTS

| EP | 1 679 032 | 7/2006 |
| EP | 2 113 274 | 11/2009 |

(Continued)

OTHER PUBLICATIONS

International Search Report for PCT/AU2012/001369, dated Jan. 22, 2013.
(Continued)

*Primary Examiner* — Annette Dixon
(74) *Attorney, Agent, or Firm* — Nixon & Vanderhye P.C.

(57) ABSTRACT

A respiratory assistance component is disclosed that changes shape when an electrical charge is provided. The amount of electrical charge that is applied may be based on values, characteristics, or user controlled parameters of the respiratory assistance system. The component may be all or part of a patient interface, a tube, a flow generator, and/or a sleep mat.

20 Claims, 27 Drawing Sheets

Related U.S. Application Data continuation of application No. 14/357,127, filed as application No. PCT/AU2012/001369 on Nov. 8, 2012, now Pat. No. 9,687,619.

(60) Provisional application No. 61/557,134, filed on Nov. 8, 2011.

(51) Int. Cl.
*A61M 16/08* (2006.01)
*A61M 16/20* (2006.01)
*A47C 31/12* (2006.01)
*A61M 16/10* (2006.01)

(52) U.S. Cl.
CPC .......... *A61M 16/024* (2017.08); *A61M 16/06* (2013.01); *A61M 16/0605* (2014.02); *A61M 16/0622* (2014.02); *A61M 16/0633* (2014.02); *A61M 16/0666* (2013.01); *A61M 16/0683* (2013.01); *A61M 16/0816* (2013.01); *A61M 16/0875* (2013.01); *A61M 16/20* (2013.01); *A61H 2201/0196* (2013.01); *A61H 2201/0207* (2013.01); *A61H 2201/0228* (2013.01); *A61H 2201/1207* (2013.01); *A61H 2201/1604* (2013.01); *A61H 2201/165* (2013.01); *A61H 2205/022* (2013.01); *A61M 16/1095* (2014.02); *A61M 16/202* (2014.02); *A61M 2016/0021* (2013.01); *A61M 2016/0027* (2013.01); *A61M 2016/0033* (2013.01); *A61M 2205/0283* (2013.01); *A61M 2205/15* (2013.01); *A61M 2205/332* (2013.01); *A61M 2205/3375* (2013.01); *A61M 2205/42* (2013.01); *A61M 2230/62* (2013.01)

(58) Field of Classification Search
CPC .......... A61B 2017/00305; A61B 2017/00318; A61B 2017/0034; A61B 2017/3433; A61B 2034/301; A61B 34/30; A61B 5/1076; A61H 2201/0196; A61H 2201/0207; A61H 2201/0228; A61H 2201/1207; A61H 2201/1604; A61H 2201/165; A61H 2205/022; A61M 16/0003; A61M 16/0057; A61M 16/024; A61M 16/04; A61M 16/0434; A61M 16/0443; A61M 16/0463; A61M 16/0488; A61M 16/06; A61M 16/0605; A61M 16/0622; A61M 16/0633; A61M 16/0666; A61M 16/0683; A61M 16/0816; A61M 16/0875; A61M 16/1095; A61M 16/20; A61M 16/202; A61M 2016/0021; A61M 2016/0027; A61M 2016/0033; A61M 2025/0024; A61M 2025/0058; A61M 2025/0161; A61M 2205/0283; A61M 2205/15; A61M 2205/332; A61M 2205/3375; A61M 2205/42; A61M 2230/62; A61M 25/00; A61M 25/0023; A61M 25/0105; A61M 25/0136; A61M 25/0138; A61M 25/0141; A61M 25/0144; A61M 25/0147; A61M 25/0158
See application file for complete search history.

(56) References Cited

U.S. PATENT DOCUMENTS

| | | |
|---|---|---|
| 5,538,000 A | 7/1996 | Rudolph |
| 5,551,419 A | 9/1996 | Froehlich |
| 7,397,166 B1 | 7/2008 | Morgan et al. |
| 7,882,842 B2 | 2/2011 | Bhat et al. |
| 9,687,619 B2* | 6/2017 | Stuebiger .......... A61M 16/0666 |
| 10,806,875 B2* | 10/2020 | Stuebiger .......... A61M 16/0875 |
| 2003/0236445 A1 | 12/2003 | Couvillon, Jr. |
| 2004/0054322 A1 | 3/2004 | Vargas |
| 2005/0011523 A1 | 1/2005 | Aylsworth et al. |
| 2006/0118117 A1 | 6/2006 | Berthon-Jones et al. |
| 2006/0169281 A1 | 8/2006 | Aylsworth et al. |
| 2007/0088322 A1* | 4/2007 | Dicarlo ............. A61M 25/0023 604/246 |
| 2007/0049852 A1 | 6/2007 | Noguchi |
| 2007/0135803 A1 | 6/2007 | Belson |
| 2007/0137653 A1 | 6/2007 | Wood |
| 2007/0219576 A1 | 9/2007 | Cangialosi |
| 2008/0027528 A1 | 1/2008 | Jagger |
| 2008/0091170 A1 | 4/2008 | Vargas |
| 2008/0208133 A1 | 8/2008 | Lieberman |
| 2009/0101153 A1 | 4/2009 | Boyden et al. |
| 2009/0177261 A1 | 7/2009 | Teoh |
| 2011/0034765 A1 | 2/2011 | Wehrheim |
| 2011/0146689 A1* | 6/2011 | Curley ............. A61M 16/0443 128/207.14 |
| 2011/0220112 A1 | 9/2011 | Connor |
| 2014/0228642 A1* | 8/2014 | Vargas ............. A61M 25/0158 600/143 |
| 2014/0311492 A1 | 10/2014 | Stuebiger |
| 2017/0239430 A1 | 8/2017 | Stuebiger et al. |

FOREIGN PATENT DOCUMENTS

| | | |
|---|---|---|
| EP | 1 902 743 | 2/2011 |
| JP | 2005-503869 | 2/2005 |
| JP | 2006-102498 | 4/2006 |
| JP | 2007-044503 | 2/2007 |
| WO | 2003/107523 | 12/2003 |
| WO | 2005/099801 | 10/2005 |
| WO | 2011128440 A1 | 10/2011 |
| WO | 2012/094426 | 7/2012 |

OTHER PUBLICATIONS

Written Opinion of the International Searching Authority, dated Jan. 22, 2013.
Patent Examination Report No. 1, issued in Australian Patent Application No. 2012334808, dated Dec. 4, 2014
European Search Report issued in European Application No. 12848263, dated Apr. 1, 2015.
Chinese Office Action issued in Application No. 201280066285.8, dated Dec. 1, 2016 with English translation.
Second Chinese Office Action issued in Application No. 201280066285. 8, dated Aug. 3, 2016 with English translation.
Japanese Office Action issued in Application No. 2014-540272, dated Oct. 31, 2016 with English translation.
European Communication in Application No. 12848263.5, dated Apr. 17, 2015 (1 page).
Response to European Communication in Application No. 12848263.5 filed, Oct. 27, 2015 (14 pages).
European Office Action in Application No. 12848263.5, dated Feb. 26, 2016 (7 pages).
Response to European Office Action in Application No. 12848263. 5, dated Jul. 6, 2016 (18 pages).
European Office Action in Application No. 12848263.5, dated Nov. 7, 2017 (8 pages).

* cited by examiner

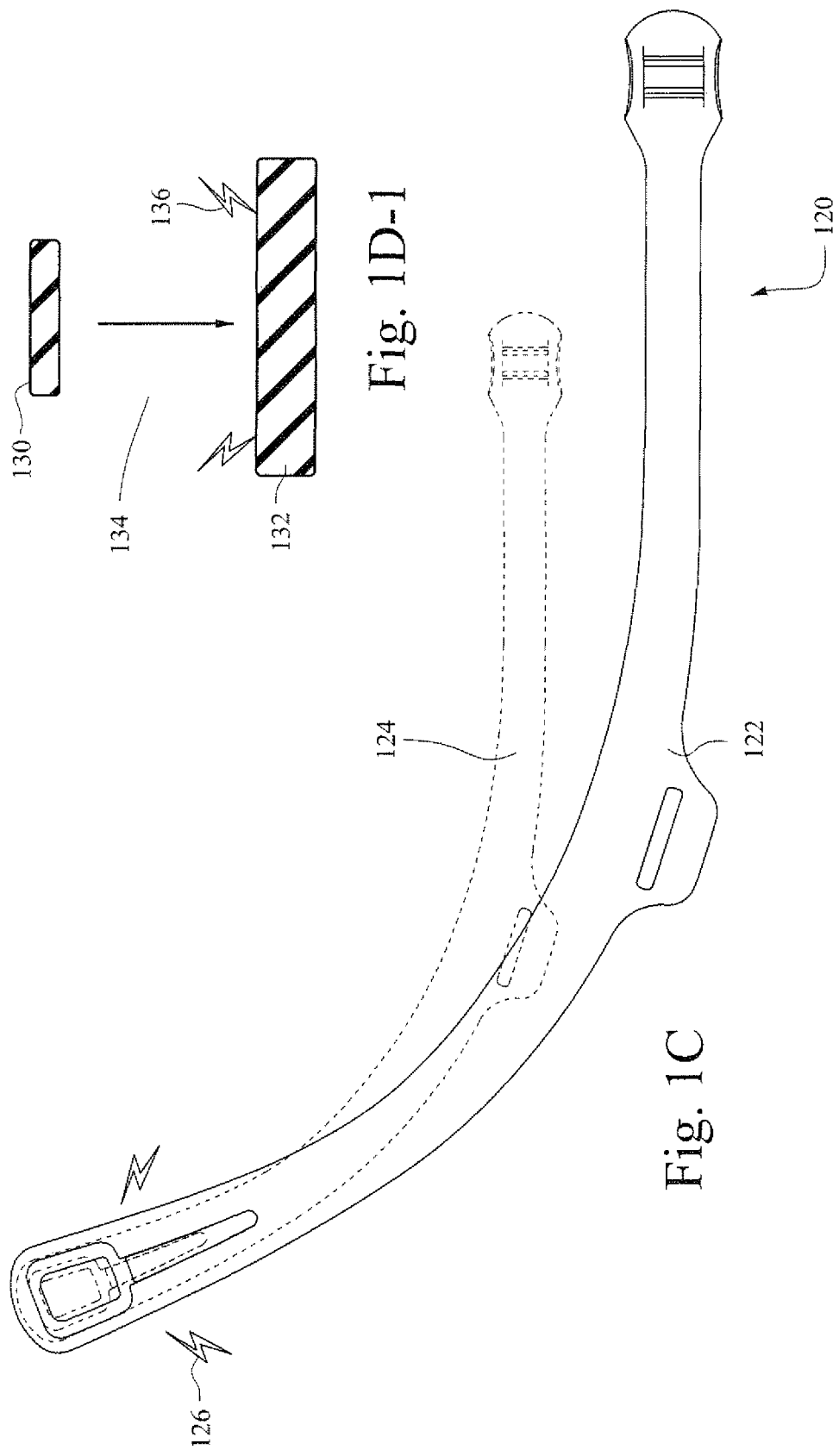

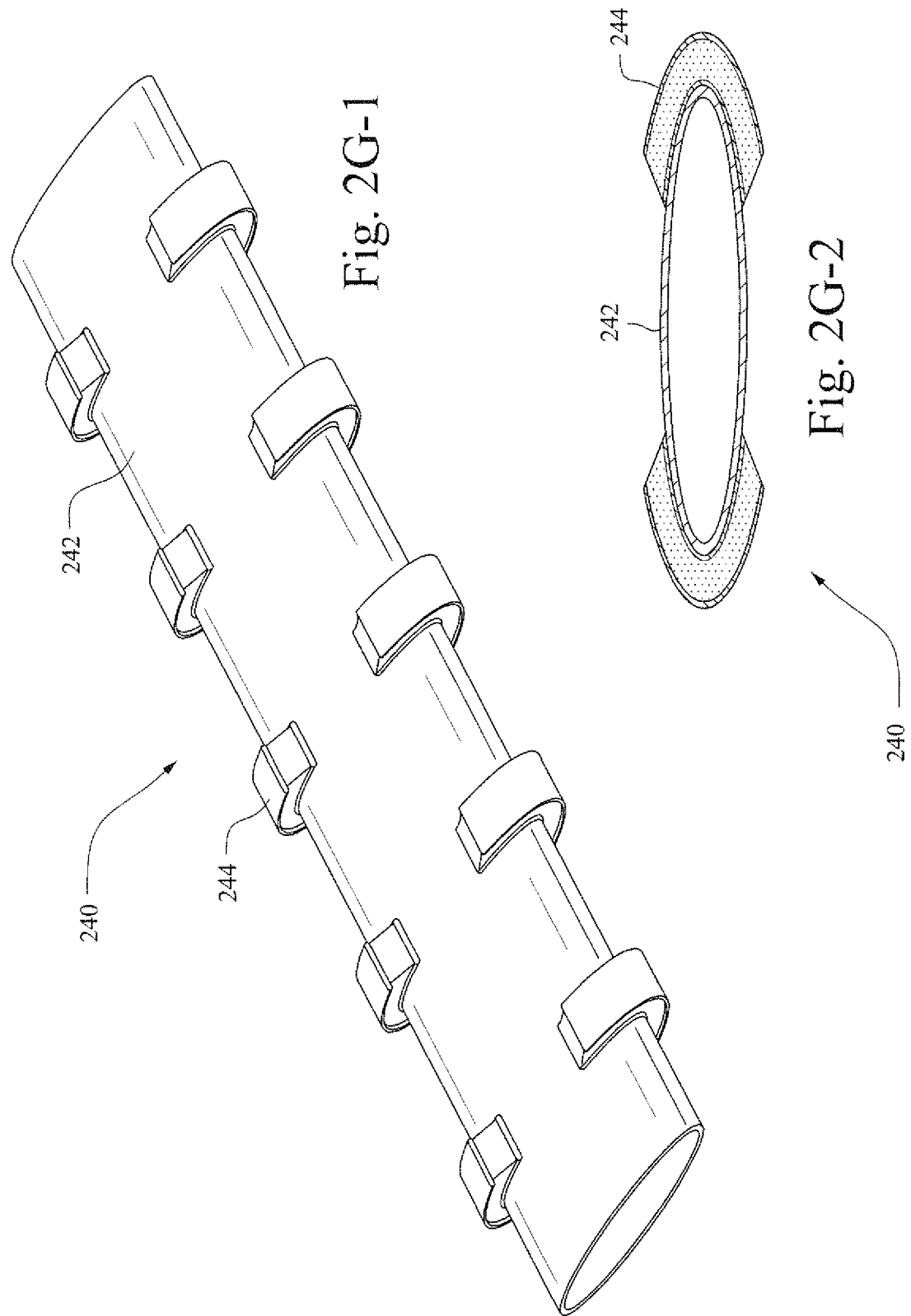

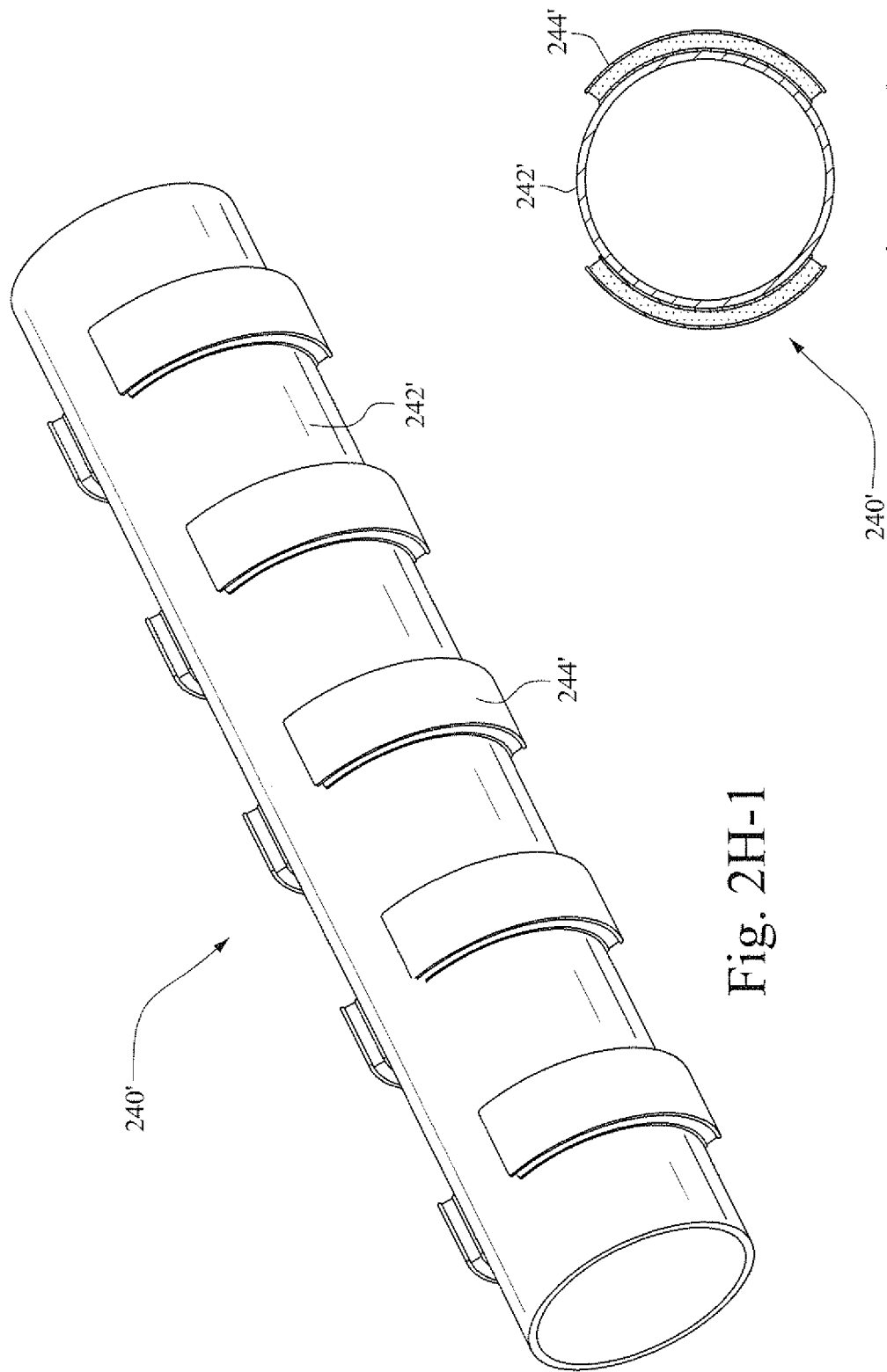

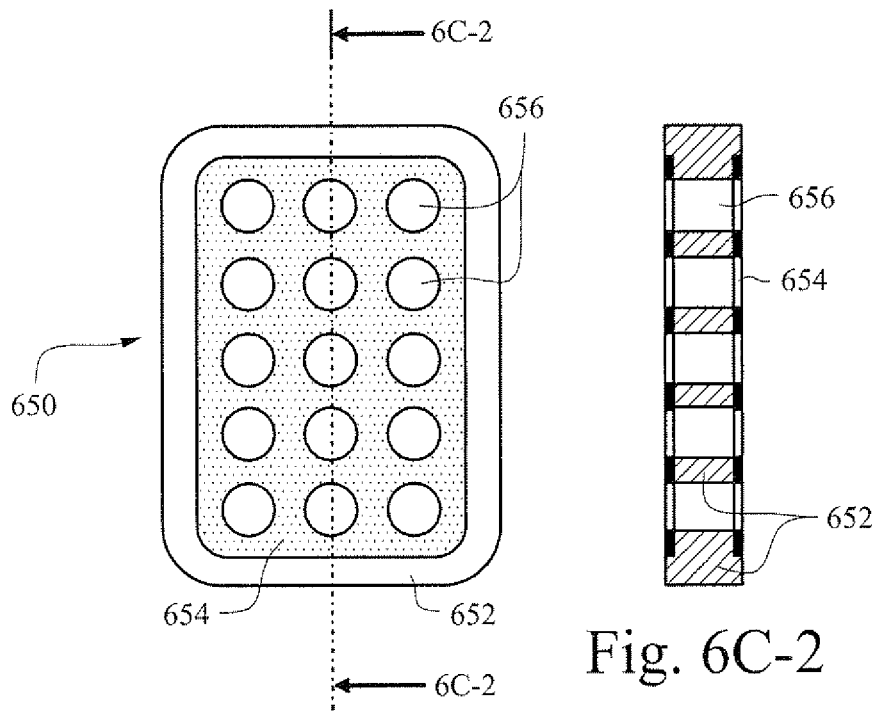
Fig. 6C-1
Fig. 6C-2
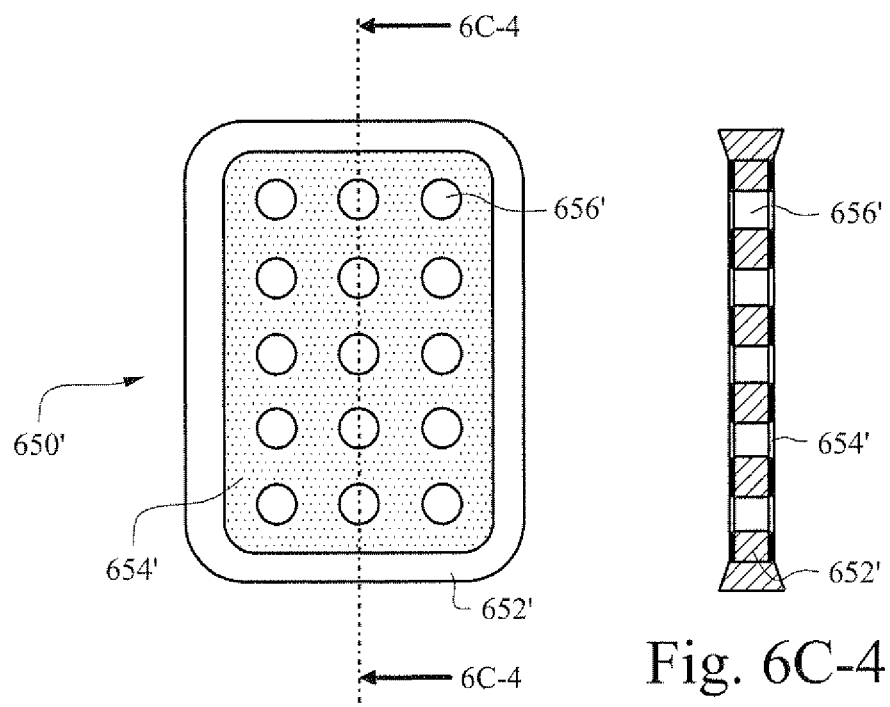
Fig. 6C-3
Fig. 6C-4

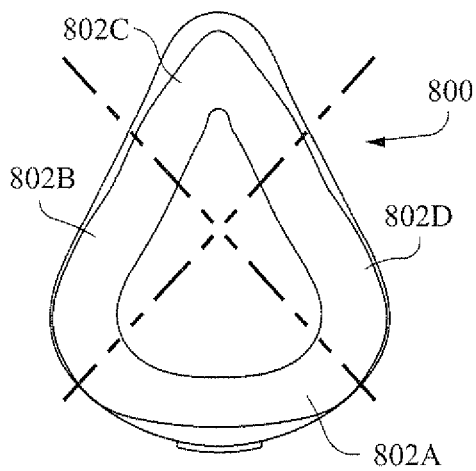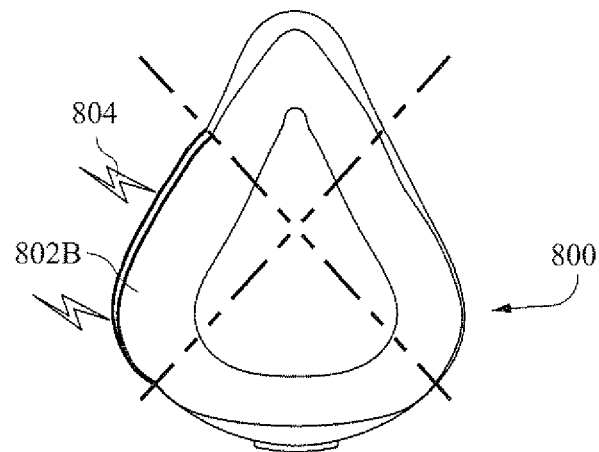
Fig. 8A
Fig. 8B
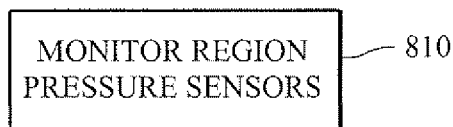
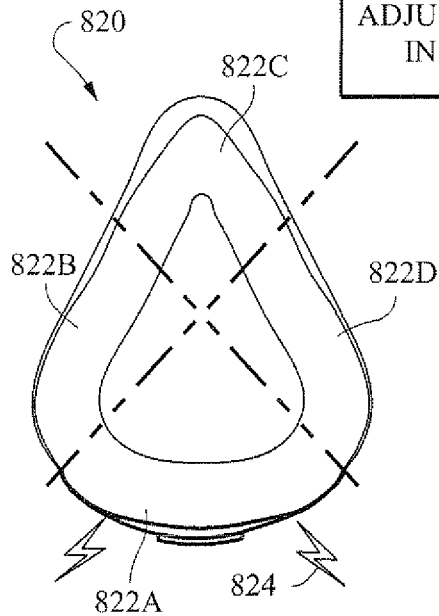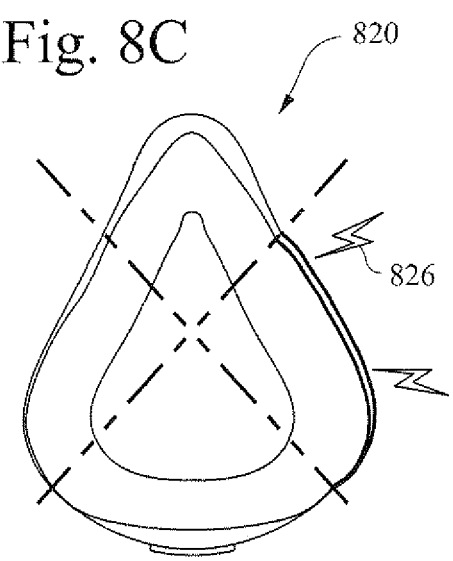
Fig. 8D
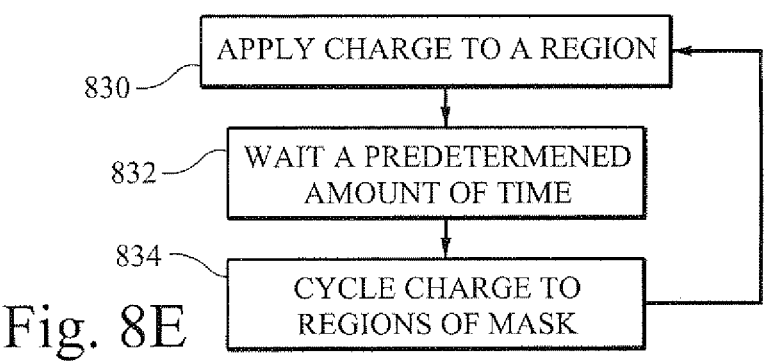
Fig. 8E

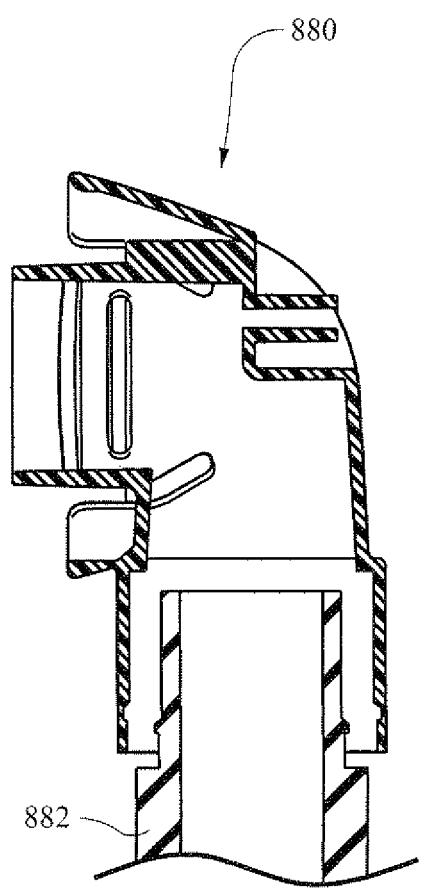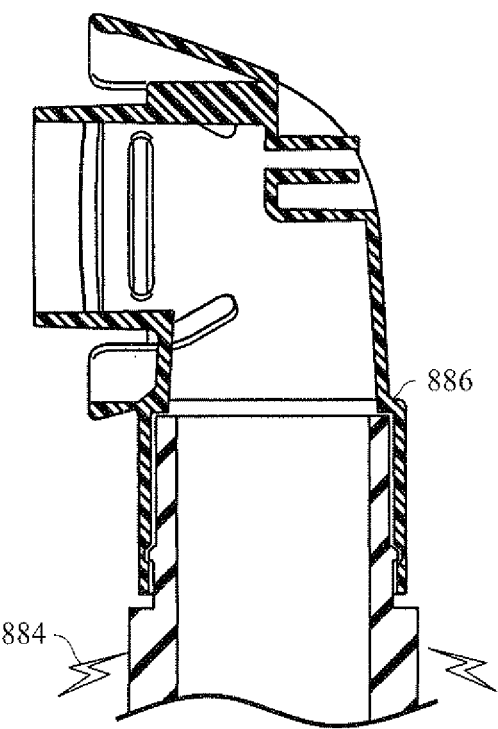
Fig. 8I-1    Fig. 8I-2

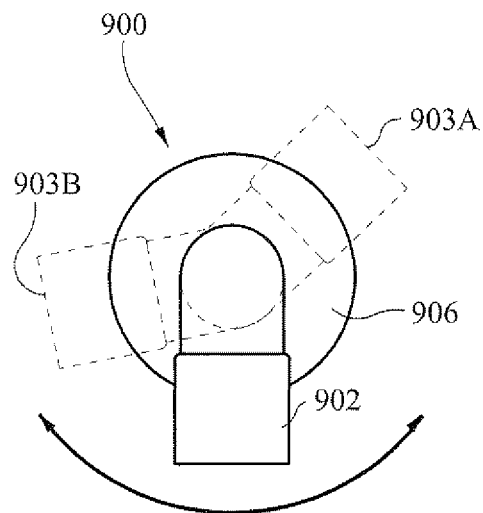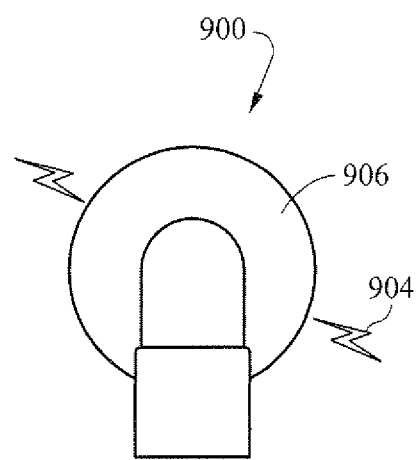
Fig. 9A      Fig. 9B
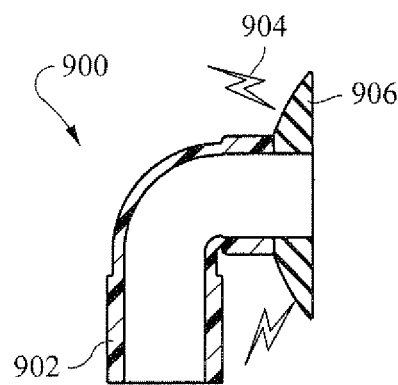
Fig. 9C

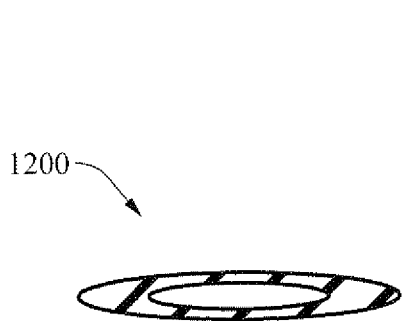
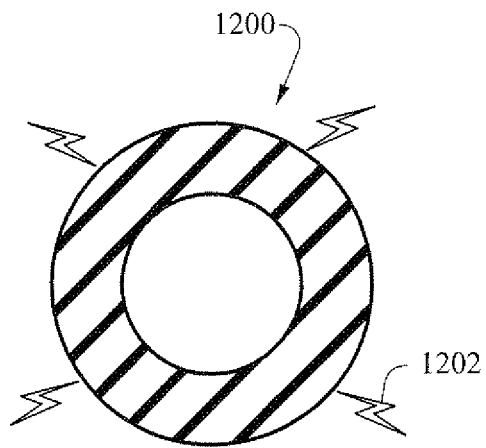
Fig. 12A
Fig. 12B
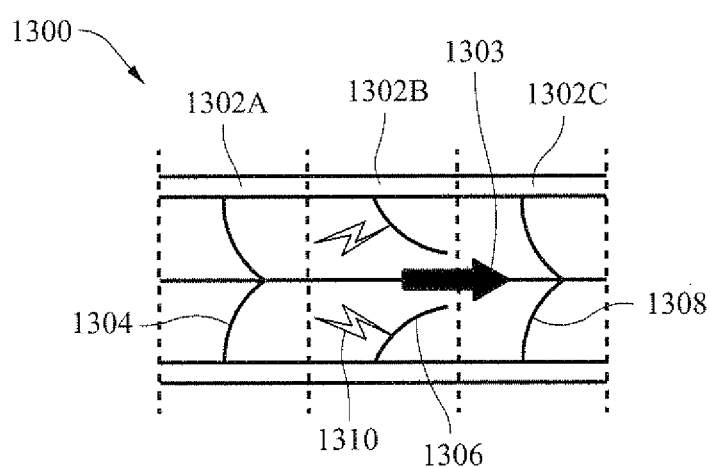
Fig. 13A

ELECTRICALLY STIMULATED RESPIRATORY ASSISTANCE COMPONENTS

CROSS-REFERENCE TO APPLICATIONS

This application is a Continuation of U.S. patent application Ser. No. 15/590,415, filed May 9, 2017, now allowed; which is a Continuation of U.S. patent application Ser. No. 14/357,127, filed May 8, 2014, now U.S. Pat. No. 9,687,619, issued Jun. 27, 2017; which is the U.S. national phase of International Application No. PCT/AU2012/001369, filed Nov. 8, 2012, which designated the U.S. and claims priority to U.S. Provisional Application No. 61/557,134, filed Nov. 8, 2011, the entire contents of each of which are hereby incorporated by reference.

FIELD

The technology herein relates to respiratory related devices and the like including at least one component that maybe electrically stimulated. More particularly, the technology herein relates to systems and methods of adjusting the size, shape, and/or other characteristics of respiratory related devices based on characteristics of a patient or other criteria.

BACKGROUND

Medical treatments for patients do not typically come in one size. Patient and environmental variables (e.g., ambient air temperature, humidity, etc) can vary how a given treatment is to be applied to a patient. One area where individual characteristics can affect medical treatment is the provision of respiratory assistance for patients. For example, in the treatment of sleep apnea or obstructive sleep apnea (OSA) via Continuous Positive Airway Pressure (CPAP). Generally, treatment involves providing a supply of air or breathable gas from a blower (sometimes referred to as a flow generator) to a patient via an air delivery conduit (e.g. a flexible tube) and a patient interface, such as, for example, a full-face or nasal mask, or nasal prongs. While treatment can be effective, there are multiple variables that if incorrectly accounted for can reduce the overall effectiveness of the treatment.

For example, the masks used in CPAP treatment should be matched to the specific characteristics of a patient's face. Masks act to provide a sealed cavity around a portion of a person's head (e.g., over the nasal and/or mouth areas of a person). However, a poorly sized mask may result in an incomplete seal being formed. An incomplete seal may lead to leaks in the mask during treatment. These leaks can lead to further negative effects. For example, the efficiency of the CPAP treatment may be reduced which may lead to further OSA episodes. Also, the leaks in the seal may cause high pitched noises to occur that may disturb others. Further, the leaks may cause skin or eye irritation on the wearer of the mask. A properly sized and fitted mask can help to avoid these problems.

Conventionally, various techniques may seek to address such problems. For example, templates may be used to determine a patient's head size or the custom mask may be created from a mold of the patient's face. However, changes in patient or environmental characteristics may reduce the effectiveness of the mask.

SUMMARY

Respiratory assistance systems may include CPAP apparatuses and/or apparatuses that facilitate a supply of pressurized breathable gas to a patient.

Respiratory assistance systems may include a patient interface with a mask portion. The mask portion may include different types of masks, for example, nasal masks, full-face masks, and nozzles (sometimes referred to as nasal pillows or puffs), nasal prongs, and nasal cannulae, etc.

Other components of a respiratory assistance system may include: 1) conduits (e.g., tubes) that may be flexible or semi-rigid; 2) straps (e.g., part of headgear of the mask or mask frame) that function to secure a patient interface; 3) anti-asphyxia valves that ensure breathable air access; 4) cushions for patient interfaces; 5) forehead cushions on a mask; 6) elbow connectors that interface with conduits; 7) sleep mats; 8) noise damping systems for flow generators; 9) splints for a patient's mouth or throat; 10) pumps such as, for example, peristaltic pumps that deliver breathable pressurized gas to a patient; 11) flow generators and their associated components; and/or 11) other components that function in assisting the provision of respiratory assistance of a patient, either in whole or in part. Other types of medical related components from outside the respiratory arts may also be used with the shape changing material described herein.

One aspect relates to forming one or more components of a respiratory assistance system out of a shape changing material that changes shape and/or size in at least one dimension associated with the material, upon electrical stimulation. The shape changing material may be an electro active polymer (EAPs) or elastomer (e.g., elastomeric in nature), for example a silicone, based material. Certain example embodiments may use different types of EAPs. For certain example embodiments, ionic EAPs may be used. For ionic EAPs, actuation is caused by the displacement of ions inside the polymer and may be carried out via a relatively decreased voltage, but an increased supply of power. Ionic EAPs may also need to be constantly energized to maintain the changed shape adopted due to electro-stimulation.

For certain example embodiments, dielectric EAPs may be used where actuation is caused by electrostatic forces between two electrodes squeezing the polymer. Such dielectric elastomers may be capable of very high strain. These EAPs may also require an increased voltage e.g., about 100 V/mm), but decreased electrical power. Also, a dielectric EAP may require little or no power to stay in a given position. In the changed position, strain levels between about 10% and 200% may be achieved. In certain example embodiments, an acrylic elastomer tape manufactured by 3M™ corporation (available under the trade name VHB™) may be capable of planar strains of more than 300% for biaxially symmetric constraints and linear strains up to 215% for uniaxial constraints. Accordingly, certain example embodiments may use dielectric polymers.

In certain example embodiments, a component of a respiratory assistance system changes between a first state and a second state. Such states may be associated with different sizes and/or shapes of the components. In certain example embodiments, the change between the first and second states of a respiratory assistance component increases the effectiveness of respiratory assistance provided to a patient. For example, a seal of a patient interface may be improved and/or controlled based on the breathing pattern of the patient.

In certain example embodiments, a size of a component and/or patient interface may be adjusted to achieve an improved fit for a given patient (e.g., based the anthropometrics of the patient). In certain example embodiments, the size of a component may be adjusted based on the breathing pattern of the patient (e.g., inhalation, exhalation, apnea severity, etc.). In certain example embodiments, a component may be adjusted based on environmental factors (e.g., the start of treatment for that night, ambient air temperature, humidity, etc.).

In certain example embodiments, the physical change in shape of a component (e.g., from the application or reduction of a charge applied to the component) may: 1) provide a safety mechanism for an anti-asphyxia valve; 2) assist in venting CO2 from a patient interface; 3) assist in reducing tube drag; 4) be done to selectively adjust components to match the characteristics of a given patient (e.g., conduits, straps, and the like); 5) function to ensure a viable airflow pathway to a patient interface from an external breathable gas source such as a flow generator; 6) improve usability of items for storing components when not in use; 7) remove air flow path blockage; 8) improved the ability of a patient to secure and remove a patient interface to their head; 9) massage the facial muscles of the patient (e.g., to reduce muscle fatigue); 10) vary the pressure that a patient interface or a part of a patient interface is applied to a patient; 11) compensate for detected leaks in mask system; 12) reduce noise associated with certain components (e.g., a flow generator); 13) prevent airway collapse or maintain an open airway; 14) act to vary a pressure associated with a breathable gas that is delivered to a patient; 15) assist or cause a patient to improve their sleeping position (e.g., to roll over).

In certain example embodiments, a default shape of a component may be the charged shape, and the "adjusted" shape may be the non-charged shape. In other words, the removal of a charge from a component may also facilitate increased patient respiratory assistance.

In certain example embodiments, the shape changing material is structured to conform to the face and/or head of a patient. The material may be a soft and/or pliable material that may be comfortably secured to the patient's head and/or face. The mask and/or components thereof may conform to different head sizes or other facial/body features while remaining comfortable for the individual patients. Thus, while the material may change shape between two or more different shapes and/or sizes, the relative comfort provided by the soft material may remain substantially unchanged.

In certain example embodiments, the soft material may be a non-metallic material (e.g., a polymer or an elastomeric material). In certain example embodiments, the shape changing material may not include any hard parts or other reinforcements (e.g., malleable wires, frames, etc). The material may be soft when electrical current is not applied and also be soft when electrical current is applied. In other words, the relative softness of the material may be maintained while the shape/size of the material is altered. In maintaining the softness of the material, patient comfort may also be maintained (e.g., because there are no hard pieces causing discomfort).

In certain example embodiments, the shape changes in the shape changing material may be multi-dimensional (e.g., two or three dimensions). For example the width and length of the material may change, but the height may remain the same.

Another aspect relates to controlling the shape changing material based on various environmental and/or patient related characteristics that may be monitored or determined. Such factors may include, for example, the breathing pattern or state of a patient, the size of the patient's head, the sleeping position of the patient, the distance a patient sleeps from a flow generator, whether or not a component is being used as part of treatment currently, detection of leaks in a mask, the assembly of the components, the sleep state of the patient, detection of breathing criteria/problems, and/or other monitored values, variables, and characteristics.

Other aspects, features, and advantages will become apparent from the following detailed description when taken in conjunction with the accompanying drawings, which are a part of this disclosure and which illustrate, by way of example, principles of this disclosure.

BRIEF DESCRIPTION OF THE DRAWINGS

The accompanying drawings facilitate an understanding of the various embodiments of this disclosure. In such drawings:

FIG. 1C is an illustrative view of an example strap or fastener;

FIGS. 2E-1-2E-3 show a perspective view and two cross-sectional views of an example conduit;

FIGS. 2F-1-2F-3 show a perspective view and two cross-sectional views of the example conduit shown in FIGS. 2E-1-2E-3, when subjected to stimulation;

FIGS. 2G-1 and 2G-2 show a perspective view and a cross-sectional view of another example conduit;

FIGS. 2H-1 and 2H-2 show a perspective view and a cross-sectional view of the example conduit shown in FIGS. 2G-1 and 2G-2, when subjected to stimulation;

FIG. 3 is a flow chart showing an example process for applying a charge in response to a detected force to change the shape of an example respiratory assistance component;

FIGS. 6B-1 and 6B-2 are illustrative cross-section views that show an example vent component;

FIGS. 6C-1 through 6C-4 show illustrative top and cross-section views of an example vent component in a non-energized (FIGS. 6C-1 and 6C-2) and in an energized (FIGS. 6C-3 and 6C-4) state, respectively;

FIGS. 8A and 8B are illustrative cross-section views of an example cushion component of a patient interface according to certain example embodiments;

FIG. 8C is a flow chart showing an example process for monitoring and adjusting an example cushion in a patient interface;

FIG. 8D shows illustrative cross-sectional views of an example cushion component of a patient interface being adjusted according to certain example embodiments;

FIG. 8E is a flow chart showing an example process of adjusting an example cushion of a patient interface;

FIGS. 8F-1 and 8F-2 are illustrative cross-section views of an example patient interface with an example cushion being adjusted based on the breathing of a patient;

FIG. 8F-3 shows an illustrative graph that may be used according to certain example embodiments to determine adjustment of an example cushion.

FIGS. 8G-1 and 8G-2 are illustrative cross-sectional views of an example patient interface with an example cushion that is fitted to two different patient with different facial characteristics;

FIGS. 8H-1 and 8H-2 are illustrative cross-sectional views of an example cushion that is integrated into an example frame of a patient interface.

FIGS. 8I-1 and 8I-2 are illustrative cross-sectional views that show an example cuff of a tube interacting with an exemplary elbow;

FIGS. 9A and 9B are illustrative views of an example elbow;

FIG. 9C is an illustrative cross-sectional view of FIG. 9B;

FIGS. 12A and 12B are illustrative cross-sectional views of an example splint;

FIG. 13A is an illustrative cross-sectional view of an example pump;

FIGS. 13B-1-13B-4 are illustrative cross-sectional views of another example pump according to certain example embodiments.

DETAILED DESCRIPTION OF ILLUSTRATED EMBODIMENTS

The following description is provided in relation to several embodiments that may share common characteristics and/or features. It is to be understood that one or more features of any of the embodiments may be combinable with one or more features of other embodiments. In addition, any single feature or combination of features in any of the embodiments may constitute an additional example.

The example embodiments described herein may relate to components and methods for providing pressurized flow of breathable air to a patient. In particular, the embodiments may relate to adjusting the size or shape of components or objects associated with a respiratory assistance system (e.g., a CPAP system). In certain examples, the change may result in changing at least one parameter of the operation of the system. The components may assist in facilitating improved patient respiratory flow. Certain example embodiments may relate sizing patient interface systems for use with a particular patient. Certain example embodiments may related to adjusting characteristics of a patient interface in response to a detected or monitored patient criteria.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

In certain example embodiments, one or more components of a respiratory assistance system may be formed out of a material that changes in shape or size in response to electrical stimulation. One example material is silicone. The silicone material may be used to fabricate or form certain components that are used in CPAP systems and the like. In certain instances, the material may be a shape-memory polymer (SMP).

In certain example embodiments, the polymer compound reacts to the application of a voltage and/or a current by contracting and/or changing its shape. The change in shape may be controlled by varying the voltage and/or the current applied to the polymer material. The polymer material may also generate a current and/or a voltage when deformed.

In certain example embodiments, the polymer compound may be electrically stimulated via a power supply that is provided from a flow generator or other powered component of a respiratory related system. In certain instances, the electrical current may be supplied from a battery or other removable and/or portable power source.

Headgear and/or Conduit

One area of patient respiratory treatment involves the delivery of breathable air through a conduit or tube to a patient interface (e.g., a mask). Different types of masks may have different types of conduits associated therewith.

Figure 1A:
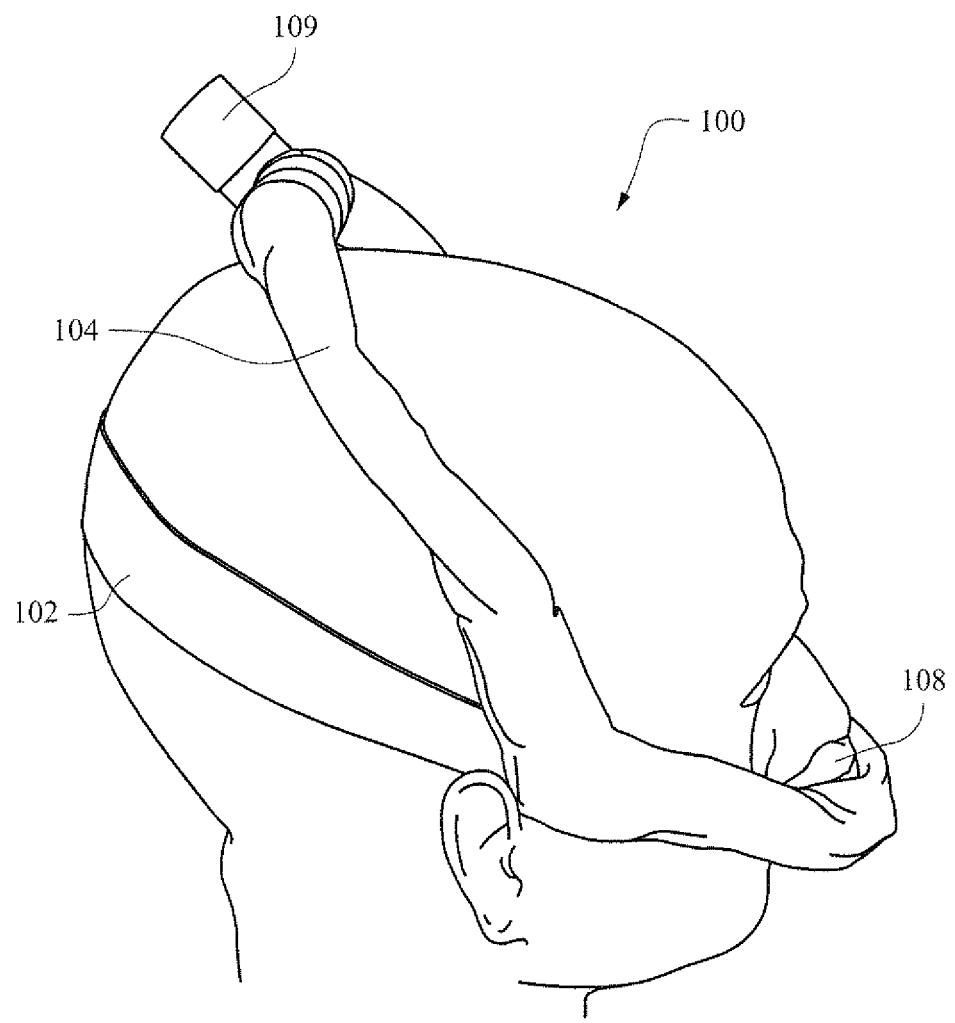
FIG. 1A is an illustrative view showing a patient wearing an example patient interface device.

FIG. 1A is an illustrative view showing a patient 100 wearing an example patient interface 108. In this example the patient interface 108 interfaces with the patient's nose (e.g., a nasal mask or an interface that seals against/in the nares of the patient). A flow of breathable gas may be provided to the patient via conduits 104 that extend from the patient interface 108, over the patient's cheeks, to the crown of the patient's head. The conduits 104 may be manufactured out of the shape changing material described herein. All or only a portion of the conduits may be formed out of the shape changing material. Straps 102 may be provided to facilitate securing the patient interface 108 to the patient. The conduits 104 may be provided on both cheeks and contact at the crown of the patient's head, when in use (e.g., during treatment). The conduit 104 from each side of the patient's head may be connected to a connector 109 that is then attached to a tube that connects to a flow generator.

Patient's typically have different sized heads. Typical techniques for addressing different sized heads may include loosing or tightening of the straps 102 or providing conduits 104 of a different length to a patient with a different sized head. In FIG. 1A, the conduits may be manufactured at a first smallest size. In this example the smallest size of conduit may fit the head of the patient 100.

Figure 1B:
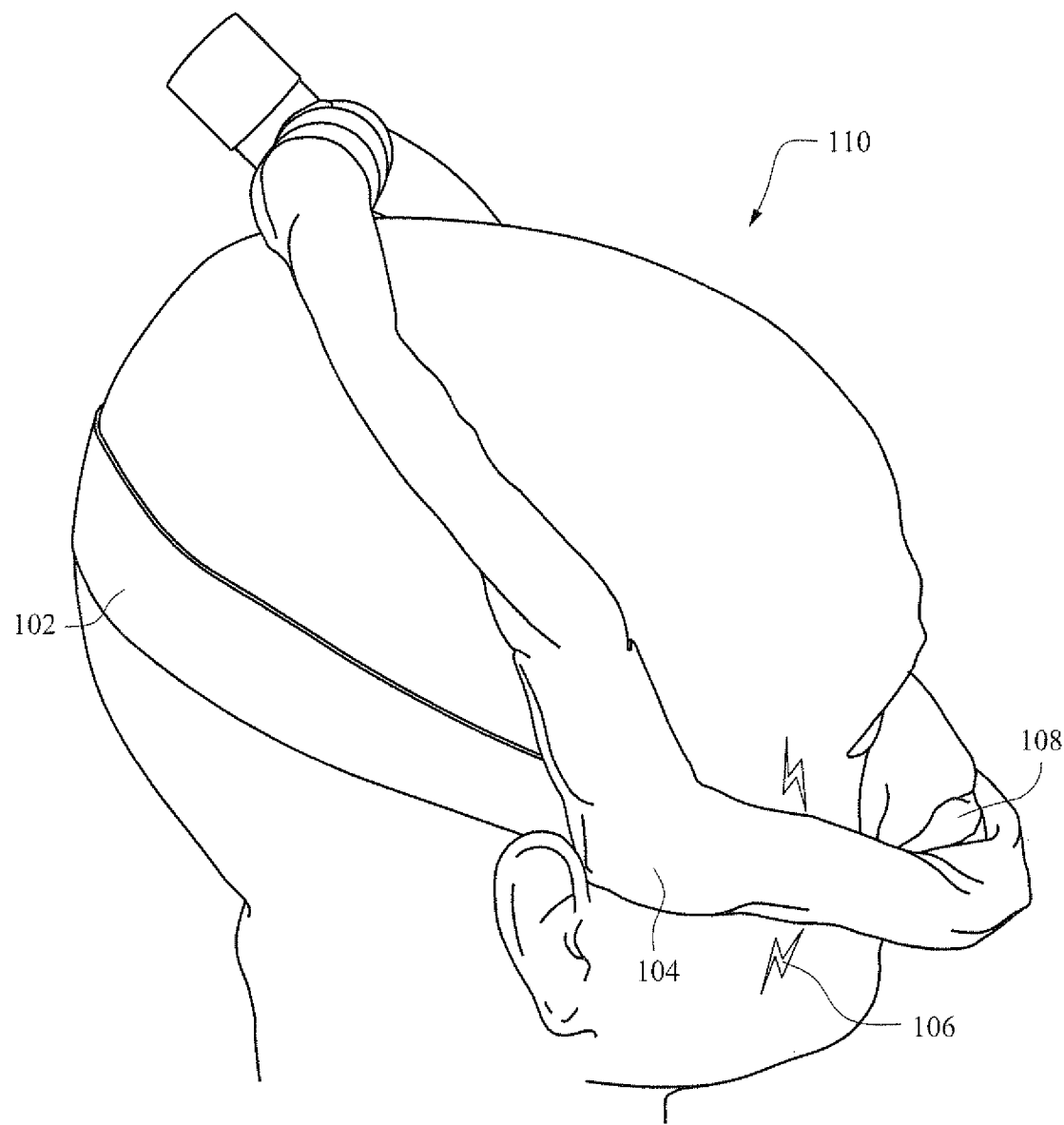
FIG. 1B is an illustrative view showing another patient wearing the example patient interface device of FIG. 1A.

FIG. 1B is an illustrative view showing another patient 110 wearing the example patient interface 108 of FIG. 1A. In this view the head size of patient 110 is larger than the head size of patient 100. Further, the mask and associated headgear (e.g., the strap 102) and the conduit 104 may be the same conduit (or the same model). However, in FIG. 1B the conduit 104 may be simulated electrically via an electrical charge 106. This charge may cause the conduit to increase in length to accommodate a larger head size due to the shape changing material changing size. Thus, a conduit may be supplied in a first size that fits a first head size of patient 100. In certain example embodiments, this first size may be a size that fits the smallest head size. However, the size of the supplied conduit may be adjusted from the first size up to a second size (e.g., patient 110). Additionally, the size may be adjusted between the first and second sizes (e.g., a middle or third size).

In certain instances, patient interfaces may include straps or other types of headgear to secure the patient interface to the head or face of the patient. By tightening the straps, a better or more effective seal may be formed. For example, strap 102 in FIG. 1A may act to hold the patient interface 108 to the nose of the patient and form a more effective seal. Thus, the strap 102 may be formed out of the shape changing material such that a charge may be applied to make the strap tighter. Alternatively, a charge may be applied to the strap before the strap is placed into position. This may allow easier placement of headgear onto a patient. Accordingly, once the patient interface, conduits, straps, etc are in their proper place, the applied charge may be reduced or turned off completely. The reduction in charge may then result in a reduction of the overall size of the strap, allowing for a patient interface to be secured to the face of a patient.

Certain example embodiments may include sensors for monitoring the tension or force being applied to the strap. Based on these values, the charge may be automatically controlled such that the strap tension is adjusted to exert a predetermined force upon the patient via the interface. In certain example embodiments, the tension or force may be a predetermined force that relates to a value which indicates that the patient interface is secure but still comfortable (e.g., not too tight). In certain example embodiments, the strap length may be controllable by the patient. For example, a dial or other control may be included with a respiratory assistance system (e.g., placed onto a flow generator). In certain example embodiments, the strap may be increased in size (e.g., by applying more charge) to facilitate removal by the patient. In certain examples, a triggering of additional charge may be done when the patient exerts a force that exceeds the current force applied by the strap. This may be sensed by a sensor to trigger additional electrical charge.

In certain example embodiments, the tightness of a strap may be adjusted based on a patient's breathing pattern or sleep state. For example, the strap may be relatively loose while the patient is awake. However, when the patient falls asleep the strap may be tightened to ensure a better seal with respect to a patient interface.

In certain example embodiments, the straps of a patient interface may be loosened during expiration by the patient. For example, the strap length may be increased or the width of the straps may be reduced. This may facilitate venting (e.g., of $CO_2$ or the like) from the patient interface. In certain example embodiments, the straps may tighten during inspiration by the patient to reduce the chance of the patient interface leaking.

FIG. 1C is an illustrative view showing an example strap or fastener. A strap 120 may be provided in a first shape 124. This may be the non-charged shape for the strap 120 that is formed out of a size adjusting material. When a charge 126 is applied to the strap 120, the strap 120 may change from the shape 124 to a shape 122. Accordingly, the size or height of the strap may be adjusted based on the applied charge.

Figures 1, 1D, 2:
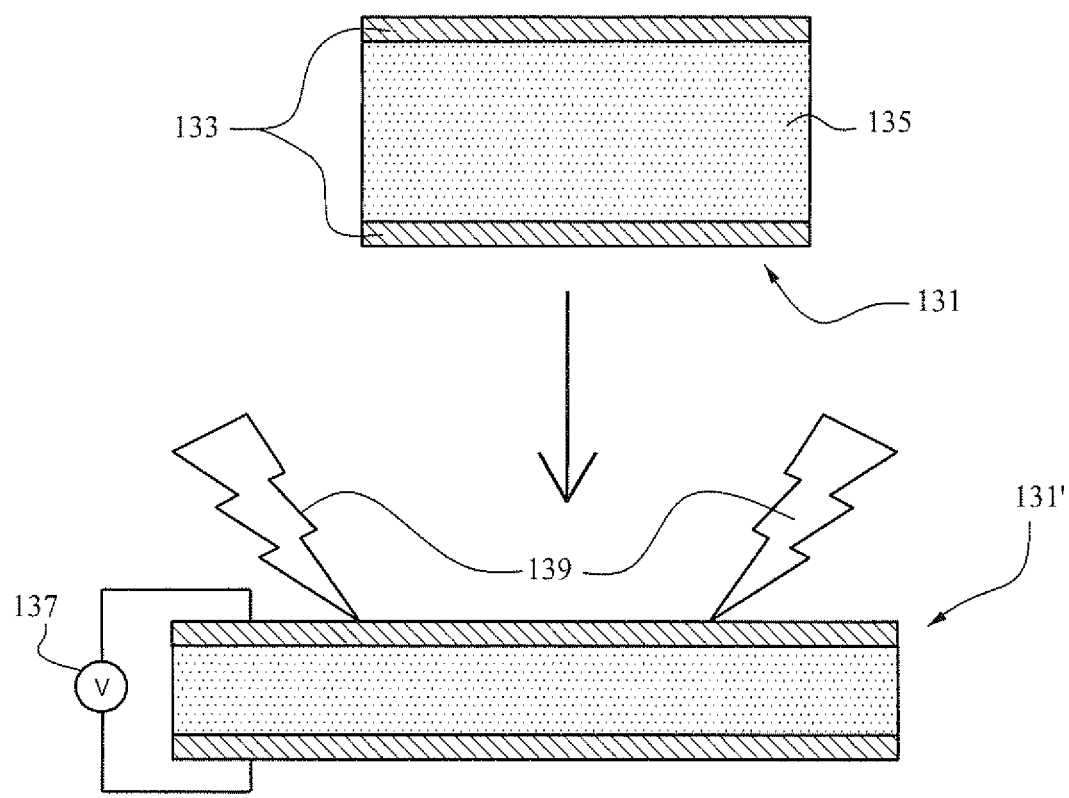
FIGS. 1D-1 and 1D-2 show illustrative cross-sectional views of polymer portions changing from a first non energized state to a second energized state after voltage has being applied in accordance with certain example embodiments.

FIG. 1D-1 is an illustrative cross-section view of a strap 134 that has a first non-charged based shape 130 that is changed into a second shape 132 when a charge 136 is applied to the strap 134. In certain example embodiments, a strap may increase in one dimension (e.g. thickness), two dimensions (e.g., width and thickness), and/or three dimensions. For example, a charge may be applied such that only the depth of the strap is adjusted while the length and/or width are not altered.

FIG. 1D-2 is another illustrative cross-sectional view of a strap or fastener according to certain example embodiments. A strap may include a dielectric polymer 131 that includes an electro active polymer layer 135 and one or more electrode layers 133. In certain example embodiments the electrode layers (e.g., two or more) may be positioned on either side of a central polymer layer. In certain example embodiments, the electrode layers 133 completely or partially encompass the polymer layer 135.

A power source 137 may be operably connected to the electrode layers and supply voltage 139 to change the shape or size of the dielectric polymer 131' by energizing or de-energizing it. It may be noted that, in this, as well as in the other embodiments described herein, the provided level of charge (e.g., voltage or current) may be controlled by a controller and applied by at least two different techniques. The voltage or current may be applied in a stepwise manner to cause a substantially stepwise change in the shape and/or the size of the polymer portion. This may include a single step, or a plurality of smaller steps of determined or predetermined voltage or current changes. Alternatively, the voltage or current may be increased (or decreased) in a manner of a continuous change, thus imparting a gradual change in the shape and/or size of the polymer. A combination between the two methods may also be applied.

Figure 1E:
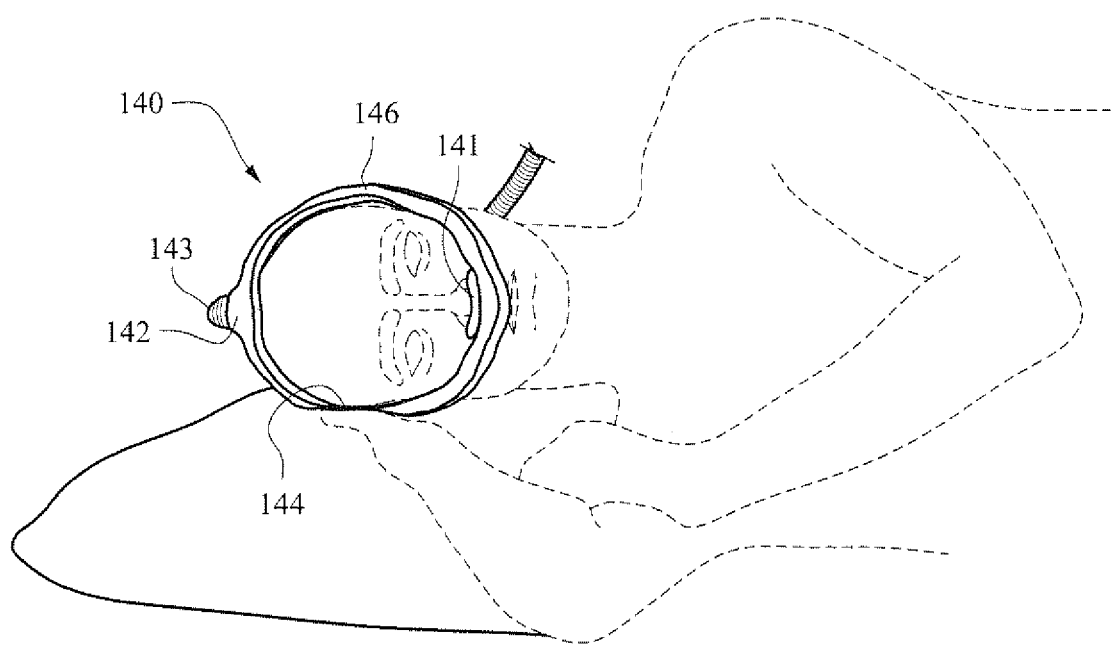
FIGS. 1E and 1F are illustrative views showing an example patient interface with electrically stimulated conduits.
Figure 1F:
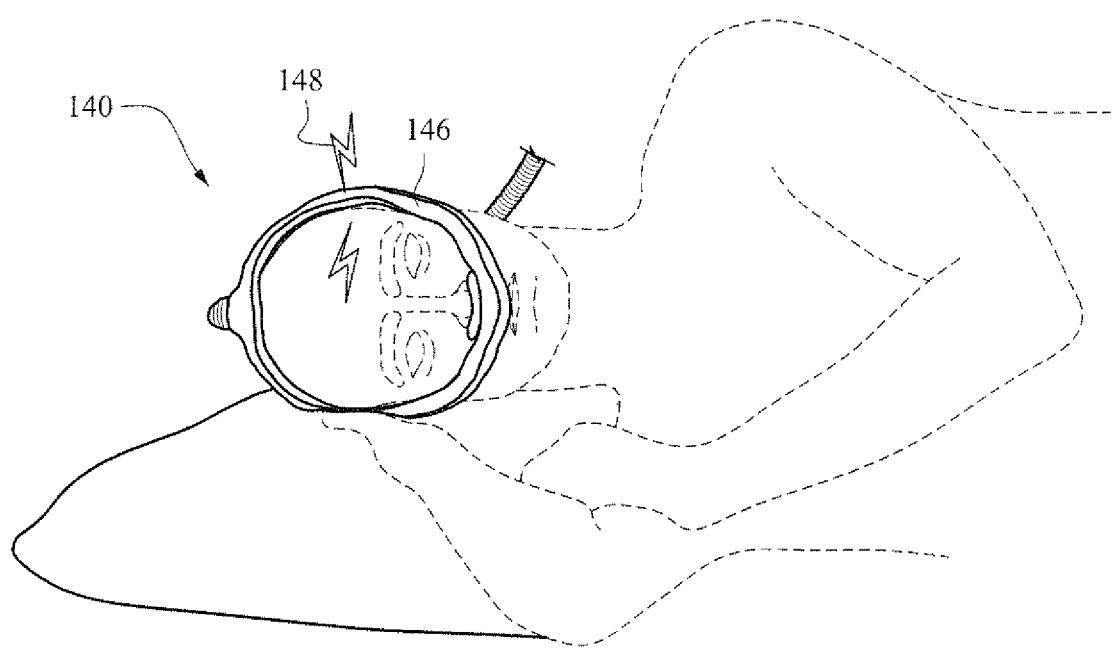

FIGS. 1E and 1F are illustrative views showing an example patient interface with electrically stimulated conduits. Here, a sleeping patient 140 is using a patient interface 141 while sleeping. The patient interface 141 has two conduits 144 and 146 that connect to the patient interface and then extend over the head of the patient to point 142. A hose or tube 143 that provides breathable air to the conduits (and subsequently to the patient) connects to the two conduits at the top point 142. The conduits 144 and 146 may be constructed such that, either of the conduits, both of the conduits, or neither of the conduits may be charged.

Some patients may sleep on their side. In certain cases, this may restrict the flow of breathable air in one of the conduits. For example, in FIGS. 1E and 1F, conduit 144 is compressed such that little or no gas may pass from the tube 143 through conduit 144 to patient interface 141. As this conduit 144 may be restricted, a charge 148 may be applied to the conduit 146 to ensure supply of breathable air to the patient. Such a charge may increase the diameter of the conduit to facilitate more air flow. In certain example embodiments, the charge may act to increase the efficiency (e.g., by removing minor kinks). In certain example embodiments, the charge may act to help prevent the conduit 146 from collapsing or otherwise impeding flow while conduit 144 is restricted. Thus, while airflow through the conduit 144 may be prevented or restricted to a certain degree, the applied charge 148 to conduit 146 may help to ensure that airflow is continuously provided to a sleeping patient.

In certain example embodiments, a collapsed conduit (e.g., 144) may have a charge applied to it in order to restore at least a portion (or all) of the airflow capacity of the previously collapsed conduit.

Figure 2A:
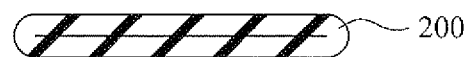
FIGS. 2A and 2B are illustrative cross-sectional views showing an example conduit.
Figure 2B:
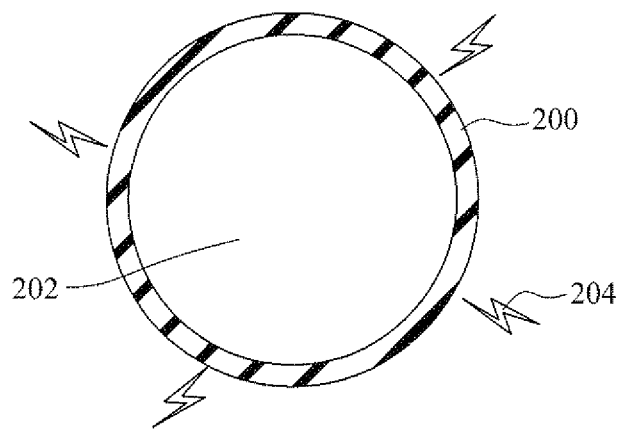

FIGS. 2A and 2B are illustrative cross-sectional views showing a conduit according to certain example embodiments. In certain instances, patients may wish to store their tubing, conduits, etc in a discrete, out of the way storage location. However, storing a fully expanded tube may be problematic both due to the overall circumference of the tube and the relative rigidity of the tube. Thus, in certain example embodiments, tubing 200 may be provided in a first small default size. In this collapsed configuration the tube is relatively flat and therefore may provide relatively easier storage options compared to the open (operational) configuration of the tube. When removed from storage and used as part of an air flow delivery system, a charge 204 may be applied to the tube such that an airflow channel 202 is created. Thus, tubes that may be typically large and/or bulky may be constructed out of the size adjusting material. The tube may be provided/shipped/sold in a first, default size that is relatively small and easy to store. However, when the tube is applied to an airflow delivery system, a charge may be applied to the tube such that the tube is brought to an open configuration and a flow of breathable gas is permitted.

The adjustment or reduction in size of certain components may also allow for easier storage for traveling. For example, the reduction in size of the conduits, tubing, straps, etc may facilitate easier packing of the components when the user is traveling by plane.

Certain example embodiments may also include straps or other headgear that are provided in an initial flat position. The flat (or easily storable) component may then have a charge applied to it in order to increase the size or shape. For example, a relatively two-dimensional shaped component (e.g., tubing 200 in FIG. 2A) may be changed to a more three-dimensional shape of increased size.

Figures 2C, 2D:
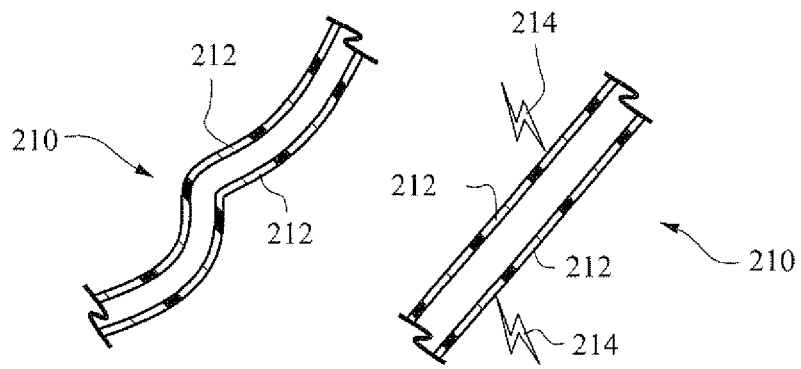
FIGS. 2C and 2D are illustrative cross-sectional views showing an example conduit.

FIGS. 2C and 2D are illustrative cross-sectional views showing an example conduit. A conduit 210 may be constructed out of a shape altering material 212. During operation the conduit may be come tangled or contorted as shown in FIG. 2C. This may cause a reduction in airflow through the conduit 210. Accordingly, a charge 214 may be applied to the conduit 210. The charge may operate to strengthen the material 212 or force the conduit 210 into a more linear shape to better facilitate airflow through the conduit. In certain example embodiments, the amount of charge may be varied or divided between sections of the conduit so that the conduit may bend or curve.

Figures 1, 2E:
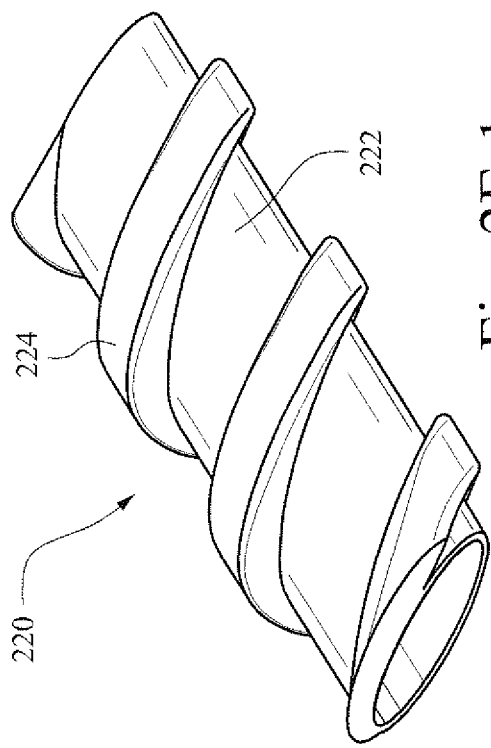
Figures 2, 2E, 3:
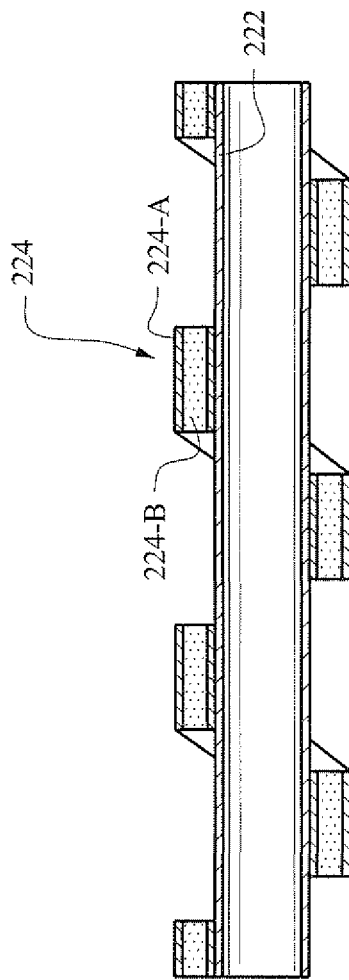
Figures 2, 2E:
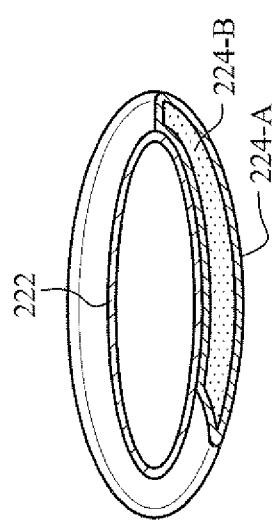
Figures 1, 2F:
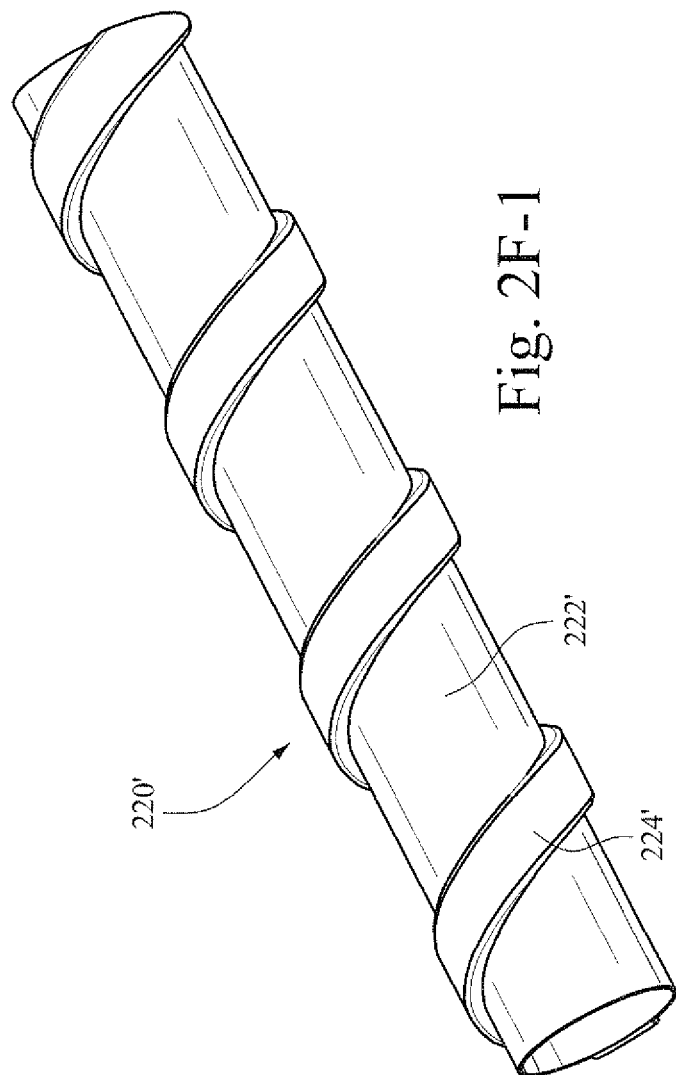
Figures 2, 2F, 3:
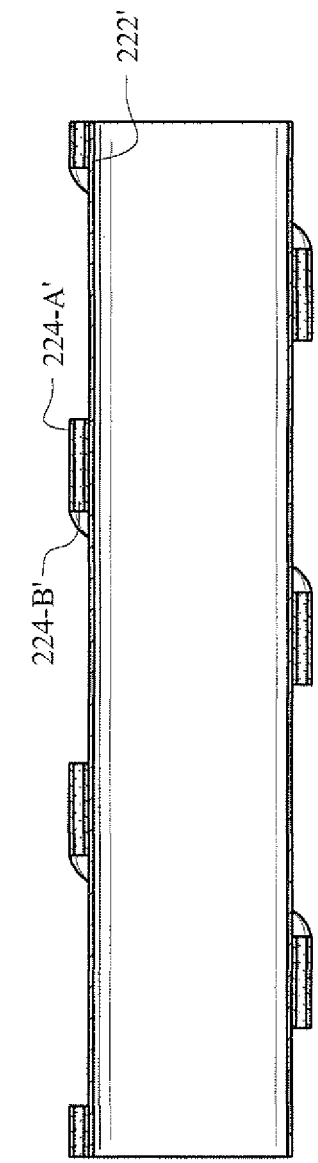
Figures 2, 2F:
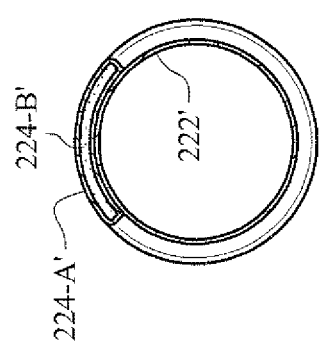
Figure 3:
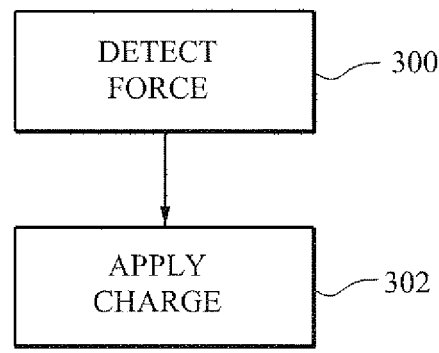

FIGS. 2E-1-2E-3 show a perspective view and two cross-sectional views of an example conduit. A polymer strip 224 that is helically formed may be attached to a membrane 222 that forms the flexible tubular body of a conduit 220. In certain example embodiments the polymer portion is in the form of a helically shaped electro active polymer strip disposed on the outside of membrane 222 that forms the longitudinally shaped body (e.g., as shown in FIG. 2E-1). In certain example embodiments, a polymer strip is disposed on the inside of the membrane. In certain example embodiments, one or more polymer strips are disposed on the inside and outside of the membrane. As shown in FIG. 2E-3, the polymer strip may include a polymer 224-B that is sandwiched, encased, or disposed between electrodes or dielectric layers 224-A.

FIGS. 2F-1-2F-3 show a perspective view and two cross-sectional views of the example conduit shown in FIGS. 2E-1-2E-3 subjected to stimulation. In an energized state, voltage is applied to electrode layer 224-A' of polymer strip 224', which causes the polymer layer 224-B' of polymer strip 224' to adjust in shape. Thus, conduit 220' and the membrane 222' thereof are expanded in a radial and/or axial direction (e.g., diameter and/or length).

As discussed herein, the voltage or current may be applied in a stepwise manner, thus causing a substantially stepwise change in the state of the conduit 220 from collapsed to open. This may include a single step, or a plurality of smaller steps in the provided voltage or current. Alternatively, the voltage or current may be increased (or decreased) in a substantially continuous manner, thus imparting a gradual change in the shape and/or size of the polymer strip 224 and gradually changing the state of the conduit 220 from collapsed to open.

FIGS. 2G-1 and 2G-2 show a perspective view and a cross-sectional view of another example conduit. Here, conduit 240 includes electro active polymer strips 244 formed as pairs along the body of the membrane 242 that forms the body of the conduit 240. Different types of distributions of the polymer strips 244 may be implemented according to various example embodiments. For example, the polymer strips may be staggered on alternative sides along the body. In the example shown in FIG. 2G-1, the polymer strips are distributed in pairs, as one or more of the pairs comprise two strips disposed on the opposite sides of the body.

In FIG. 2G-2 the energized configuration of the conduit 240' is shown. The polymer strips 244' are supplied with a voltage which causes the polymer strips to expand, thereby stretching the membrane 242' and the conduit 240' radially. In certain example embodiments, a longitudinal polymer strip may be provided along the length of the membrane to provide extension in axial direction (e.g., along the length of the conduit).

FIG. 3 is a flow chart showing an example process for applying a charge in response to a detected force. The applied charge may act to change the shape of an example respiratory assistance component. In certain example embodiments, a tube may be provided in a first "relaxed" position (e.g., no charge applied). A sensor may be implemented to detect when excessive force or tube drag occurs. For example, the tube may become tangled. Upon sensing an increase in force applied to the tube (step 300) a charge may be activated (step 302) to electrically stimulate the tube and cause the tube to increase in size (e.g., length only) and help prevent destabilization of a patient interface secured to a patient (e.g., tube drag that may be translated to the mask to pull the mask out of place).

Vents/AAV

Figure 4A:
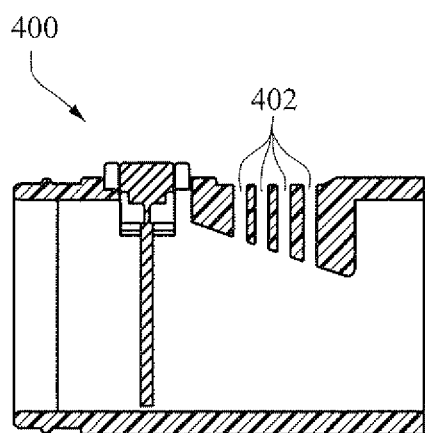
FIGS. 4A and 4B are illustrative cross-sectional views that show an exemplary vent.
Figure 4B:
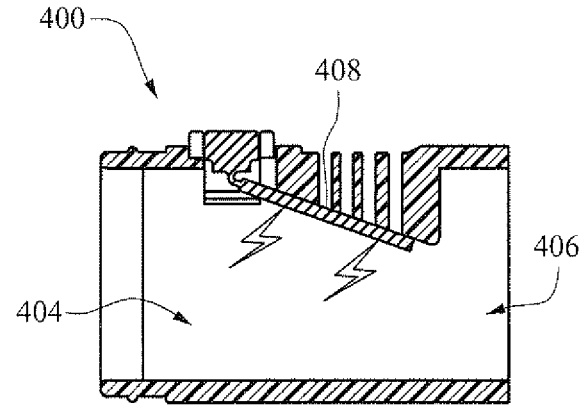

FIGS. 4A and 4B are illustrative cross-sectional views that show an exemplary anti-asphyxia vent according to certain example embodiments. In certain instances, an anti-asphyxia valve 400 may be supplied on or with a patient interface. A first operational mode is shown in FIG. 4B. Here, a flap 408 is movable against one or more openings 402 to close the openings. Accordingly, gas may flow from 404 (from the flow generator) to 406 (towards the mouth or nose of the patient). The flap 408 may be movable against the one or more openings via a charge such that it is biased to a first position and closes off the one or more openings 402.

The flap 408 may also change to a second position shown in FIG. 4A. For example, if the flow generator fails, the charge to the flap 408 may be terminated (e.g., because power is no longer provided). In this position the one or more openings 402 may be open and allow air to flow from the patient end 406 to the outside atmosphere through the one or more openings 402 and vice versa. Accordingly, the flap 408 may function as an anti-asphyxia valve (AAV).

Figure 4C:
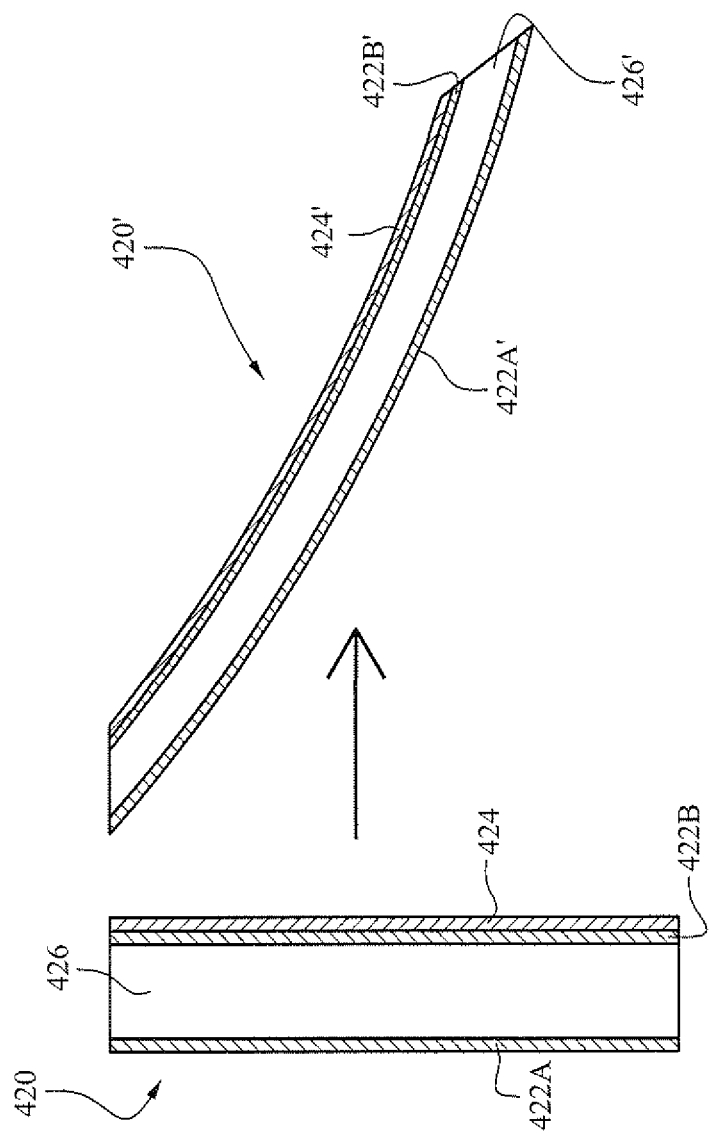
FIG. 4C shows cross-sectional views of a flap, in a non-energized state and in an energized state, according to certain example embodiments.

FIG. 4C shows a cross-sectional view of flap according to certain example embodiments (e.g., that may be implemented with the anti-asphyxia vent illustrated in FIGS. 4A and 4B). The example flap 420 shown in FIG. 4C may be implemented with dielectric active polymer. The flap 420 includes electrodes 422A and 422B between which a polymer layer 426 is disposed. It will be appreciated that the electrodes may be any type of flexible electro conductive material, such as, for example a material based on graphite films. In this example, a constraining layer is disposed to the polymer (e.g., the electrodes and/or the polymer) to limit expansion of the polymer in one or more dimensions. The constraining layer may include materials that generally do not alter their shape while the polymer's shape is transformed (e.g., any material that is flexible but not extensible, such as non-stretchable textile materials). In FIG. 4C, a constraining layer 424 is disposed to constrain the length (e.g., height) dimension of the polymer. As a result, once a voltage is applied to electrodes 422A' and 422B', the polymer 426' attempts to expand but its expansion is limited by the constraining layer 424'. Accordingly, the flap 420' may twist on the constrained side, which is the side of the constraining layer, to thereby curve or otherwise change in position. The change of the flap from a straight configuration to a bent configuration may effectively move the flap to a new position.

Figure 5:
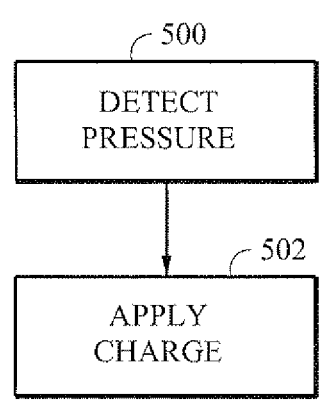
FIG. 5 is a flow chart showing an example process for applying a charge in response to a detected pressure to change the shape of an example respiratory assistance component.

FIG. 5 is a flow chart showing an example process for applying a charge in response to a detected pressure. The change may change the shape of an example respiratory assistance component. In certain example embodiments, a flap may function as a constant flow flap. A charge provided to the flap may be controlled by the flow generator. The amount of charge may be proportional to the pressure (step 500) being supplied or detected at the mask. In other words, like a constant flow valve, the valve may close vent holes at higher pressures by applying more charge (step 502). In certain example embodiments, such techniques may be applied with bi-level CPAP therapy.

Figure 6A:
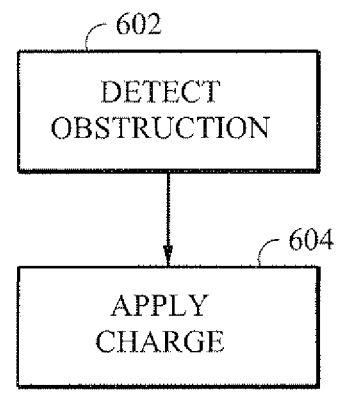
FIG. 6A is a flow chart showing an example process for applying a charge in response to a detected obstruction to change the shape of an example respiratory assistance component.

Certain example embodiments may act to correct blockage in a vent. FIG. 6A is a flow chart of an example process for applying a charge in response to a detected obstruction. The charge may change the shape of an example respiratory assistance component. For example, a sensor or other device may be used to monitor or determine if a vent is blocked (step 602). Upon detection of blockage at or in the vent, a charge may be applied (step 604) to the vent that is constructed out of the shape changing material. As a result of the charge, the vent may change shape and expel the foreign object or objects blocking the vent (e.g., through widening the vent hole). For example, water build up as a result of humidified air may result in complete or partial blockage of the vent holes of a tube or patient interface. In certain example embodiments, the holes may be reduced in sized to facilitate the removal of water (or other blockage) from a passage. Specifically, by reducing the size of the holes, the object in the hole or passage may be forced out by the decreasing diameter of the holes.

Figures 1, 6B:
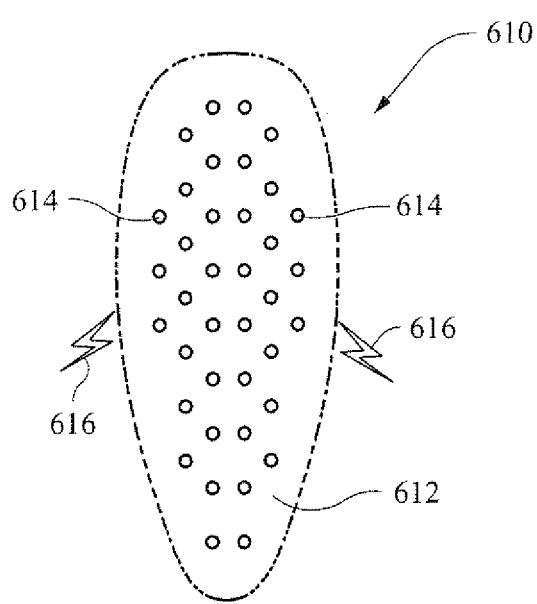
Figures 2, 6B:
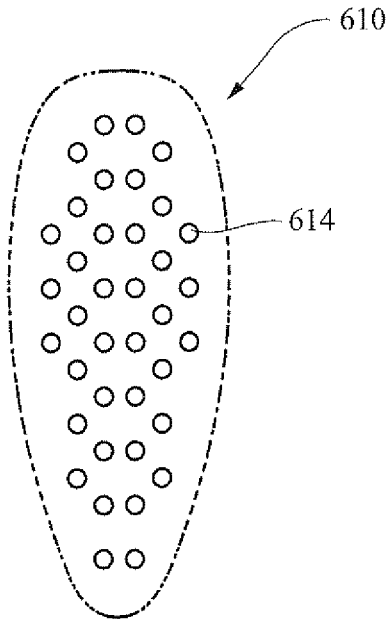

FIGS. 6B-1 and 6B-2 are illustrative cross-section views that show an example vent component. A vent 610 may include one or more holes 614. The vent may be formed out of the shape changing material 612. In a first operating mode, a charge 616 may be applied to the material 612. The charge 616 may cause the material to expand, and close or shrink the holes 614 (or vice versa). The charge 616 may be reduced or eliminated. In such and occurrence, the holes 614 may increase in size as the material 612 comprising the vent 610 shrinks. Increasing the size of the holes 614 may facilitate the removal of obstructions from the vent because the blocking objects may move more easily through the larger vent holes. In certain example embodiments, a change in hole size may be controlled by different levels of a charge to the shape changing material 612.

In certain example embodiments, a vent may be operated such that if the vent is detected as being blocked, a charge could be sent to the vent. The resulting change in shape of the vent may act to expel the foreign objects blocking the vent (e.g., water from the humidified air inside the mask).

FIGS. 6C-1 and 6C-2 respectively show illustrative top and cross-sectional views of an example vent component. FIG. 6C-1 illustrates a non-energized state of an example vent 650 that includes a dielectric polymer layer 652 disposed between electrodes 654. The vent includes vent openings 656. When the vent 650' is energized via electrodes 654' the polymer 652' expands. As a result, the openings 656' in the energized state of the polymer, shown in FIGS. 6C-3 and 6C-4, have a decreased diameter and provide decreased airflow.

Forehead Support

Figure 7A:
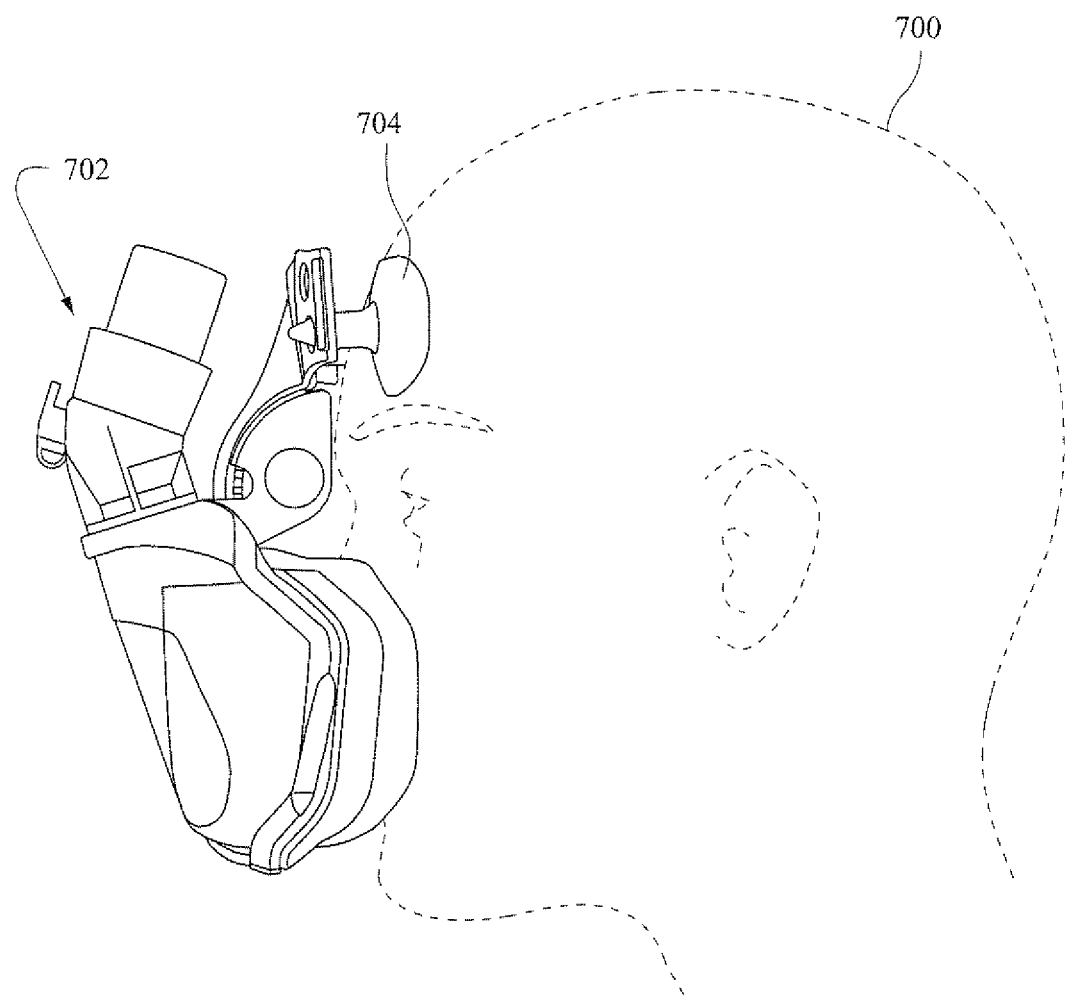
FIGS. 7A and 7B are illustrative views that show an example patient interface with an adjustable example forehead support component.
Figure 7B:
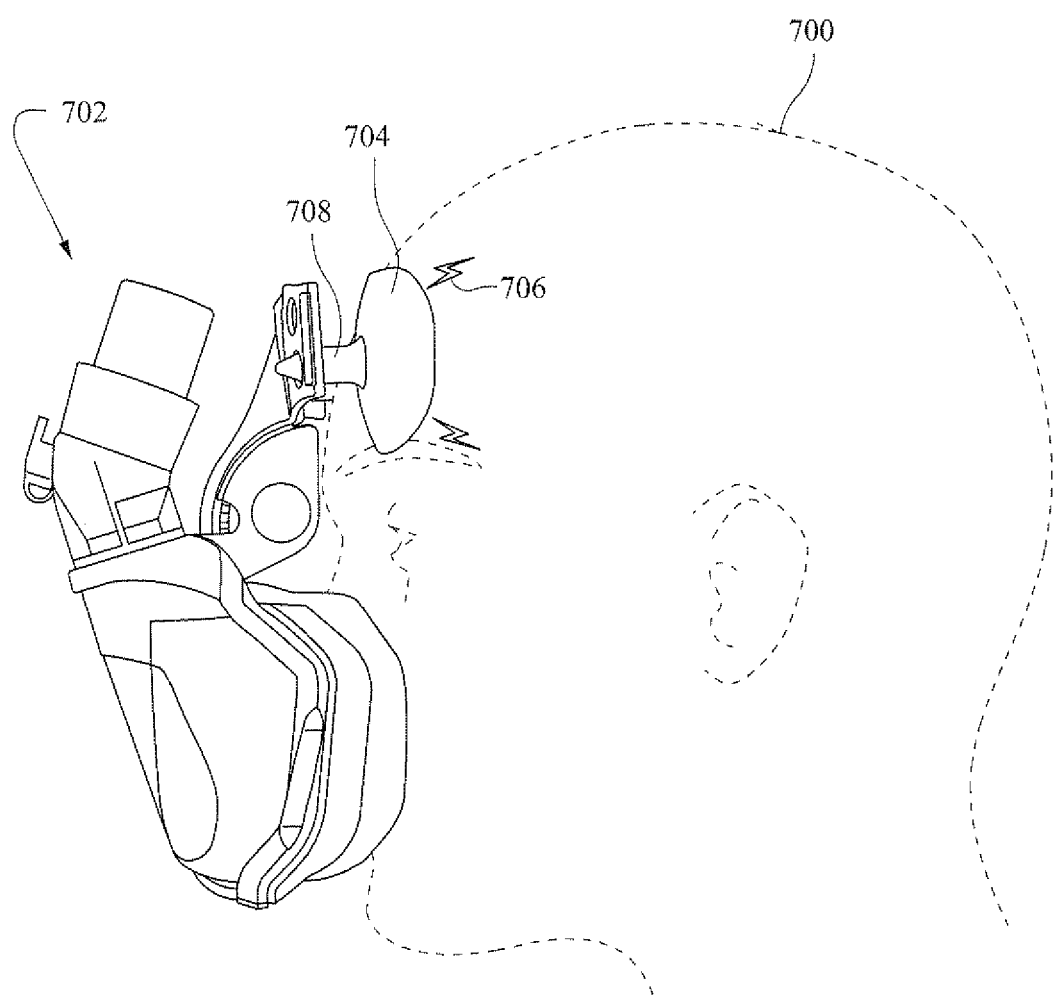

FIGS. 7A and 7B are illustrative views that show an example patient interface with an adjustable example forehead support component. A patient interface 702 is provided to a patient 700. Forehead support pads 704 may be structured to interface with the forehead of the patient 700. The position of the forehead support pads 704 in relation to the patient's head may be adjusted by applying a charge 706 to the forehead pads 704. The applied charge may cause the forehead pads 704 to become larger as shown in FIG. 7B. By increasing in size, the forehead pads may come into contact with the head (e.g., forehead) of the patient 700. A hinge, such as a living hinge, may be supplied at 708 to facilitate rotational movement of the forehead pads 704 with respect to the head of the patient 700

When the patient is done with the mask (e.g., after waking up), the charge 706 may be turned off by the patient to facilitate removal of the patient interface 702 from the head of the patient. In other words, by removing the charge applied to the forehead pads 704, the pads 704 may shrink and no longer contact the forehead of the patient. In certain example embodiments, the forehead pad may be one pad. However, in other example embodiments, the forehead pad may be two or more pads.

Cushion

The cushion component of a patient interface may also be constructed out of a shape changing material. FIGS. 8A and 8B are illustrative cross-section views of an example cushion component 800 of a patient interface according to certain example embodiments. FIG. 8C is a flow chart showing an example process for monitoring and/or adjusting an example cushion of a patient interface. In certain example embodiments, the cushion may be divided into a number of sections (802A, 802B, 802C, and 802D). Each of the sections may actively monitor the pressure applied to the cushion in that area. For example, a pressure sensor or transducer may be supplied in one or more of the sections. In certain example embodiments, a microphone may be employed. In any event, a detection unit may be used to monitor the one or more sections of the cushion (step 810). When a leak in the cushion is detected in a particular area, such as 802B in FIG. 8B, a charge 804 may be applied to that particular area (step 812). The resulting charge may act to increase the size of the cushion and increase the effectiveness of the seal formed by the cushion (e.g., by closing a leak).

FIG. 8D shows illustrative cross-sectional views of an example cushion component of a patient interface being adjusted according to certain example embodiments. Here, a cushion 820 may be setup such that the cushion 820 may have charges pulsed or otherwise distributed across the cushion areas 822A, 822B, 822C, and 822D. Thus, the amount of force exerted on the patients face may be periodically adjusted by rotating the application of charges to the multiple cushion regions. For example, the cushion may start off with a pulse 824 at the mouth region, and then a pulse 826 may be applied to the right cheek region 822D. This type of setup may function to rest areas of a patient's face, thereby making the mask more comfortable for prolonged use.

FIG. 8E is a flow chart showing an example process of adjusting an example cushion of a patient interface. In step 830, a charge is applied to a particular region. After a predetermined period of time in step 832, a new region (or regions) is selected in 834 and the process of applying the charge is renewed to the selected region. In certain example embodiments, the selected region may be based on a predetermined pattern. In certain example embodiments, the selected region may be selected based on some additional determinations (e.g., as discussed above with respect to, for example, FIG. 8C). In certain example embodiments, the selected region may be randomly picked from among the one or more regions, thus forming one or more sub-regions. In certain example embodiments, two or more pulses may be applied in a temporally overlapping manner. For example, regions 822B and 822D may both have a charge applied at the same time.

In certain example embodiments, additional criteria may be supplied by a user or automated control unit (e.g., that includes a processor or other type of circuitry) in order to control how the cycling operation occurs. For example, the user may setup how quickly the cycle occurs. In certain example embodiments, the user may set up the pattern of the cycle. For example 822A→822C→822D→822B→822A. In certain example embodiments, the time that a charge is applied to a given area may be the same for all areas or may vary between areas. In certain example embodiments, sensors and/or a processing system may monitor the cycling charges and adjust the cycle based on a predetermined criterion (or set of criteria) that may be based on at least one user configurable variable. For example, the cycle may slow down after a certain amount of time. The cycle rate may be adjusted linearly or otherwise (e.g., exponentially). In an example, the cycle rate may be adjusted when a patient is determined to be sleeping. Based on this determination the rate may be increased, reduced, or kept the same. In certain example embodiments, the cycling process may also operate to massage the face of the user. For certain patient's, this may help to increase sleep quality or the ability of a user to fall asleep.

In certain instances, a proper seal may be implemented in order to facilitate breathing assistance to a patient. However, sealing a mask onto the face or a portion of a patient's face may require a certain amount of pressure to be applied to the face. As patients typically wear a mask or other patient interface over multiple hours (e.g., while sleeping), this constant pressure may be tiring for the face of the patient (e.g., facial muscles).

Figures 1, 8F:
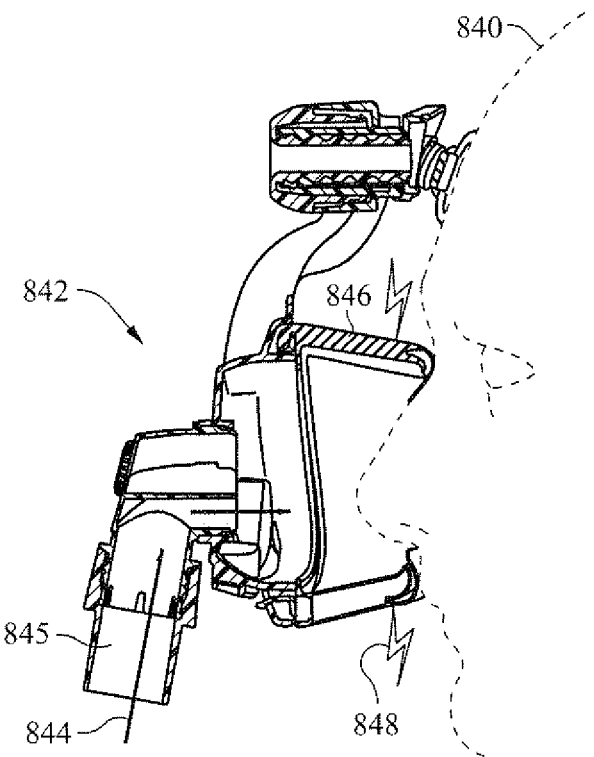
Figures 2, 8F:
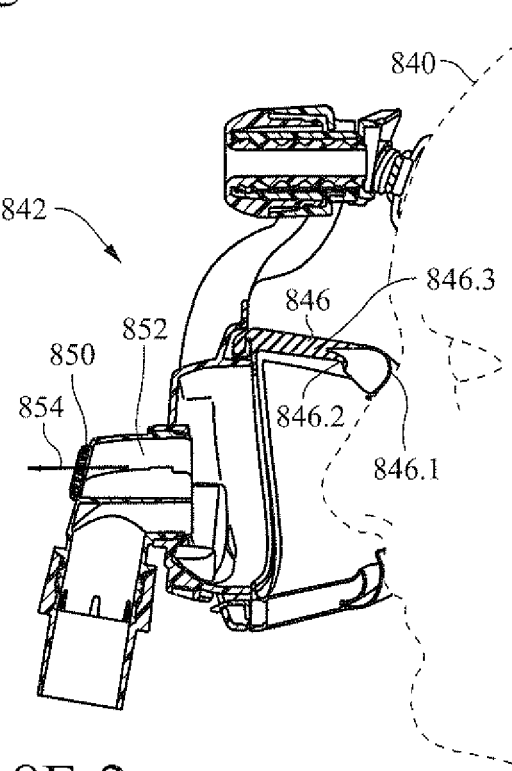
Figures 3, 8F:
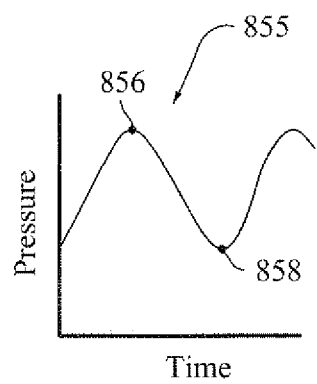

FIGS. 8F-1 and 8F-2 are illustrative cross-section views of an example patient interface with an example cushion being adjusted based on the breathing of a patient. A patient interface 842 may provide a seal to encompass the nose and/or mouth of a patient 840. The seal may be implemented or supported by applying a charge 848 to a shape changing material 846 that is part of the patient interface. For example, a charge may be applied to sealing membrane 846.1, under cushion 846.2, and/or cushion side walls 846.3. This charge may increase the effectiveness (to varying degrees) of the seal. In this example, the charge 848 may be applied to the seal (e.g., shape changing material 846) when the patient is inhaling 844 through a tube 845 that is connected to a flow generator or other airflow device.

In FIG. 8F-2 the patient 840 exhales via an airflow path 854 that is provided through chamber 852 and through vent holes 850. When the patient exhales, the charge 848 shown in FIG. 8F-1 may be turned off (or reduced) so that the cushion no longer contacts the face or contacts the face with a lower force. The reduction in force applied to the face of the patient may allow the face (e.g., facial muscles) to "rest" during exhalation.

FIG. 8F-3 shows an illustrative graph that may be used according to certain example embodiments to determine adjustment of a respiratory assistance component. A determination of when to apply a charge to a patient interface may be based on pressure and/or flow characteristics that are monitored during the breathing process of the patient. Graph 855 shows a pressure versus time graph. In certain example embodiments, analysis of such a graph may help to determine when a charge is to be applied and when a charge may be reduced or turned off. Thus, at point 856 the charge may be applied when a patient inhales. When the graph advances to point 858 at the patient exhales, the charge may be reduced or removed. The removal of the charge may increase the ease by which patient may exhale. In certain instances, the removal of the charge may allow the facial muscles of the patient to rest during expiration. In certain example embodiments, a ratio of charge percentage to detected pressure may be implemented. For example, as pressure increases (e.g., inspiration) the applied charge may be correspondingly increased. Conversely, as pressure drops (e.g., during exhalation) an applied charge may be reduced (e.g., gradually) corresponding to the drop in pressure. In certain example embodiments, other parameters may be monitored. For example, a flow rate of air through a given portion of a mask or the patient may be measured. In certain example embodiments, a pressure sensor, flow sensor, or the like may be disposed in the mask, tube, or other component that is used for respiratory assistance to a patient. The readings from such a sensor may be used to help determine when a charge may be applied and the level of the charge to be applied.

In certain example embodiments, other components of a respiratory assistance system may be adjusted based on a detected expiration/inspiration state of a patient. For example, the vent holes 850 may be increased in size during expiration to facilitate patient expiration, vent $CO_2$, etc. In certain example embodiments, a patient interface may be used as part of CPAP treatment. In such an instance, the amount of effort exerted by a patient to exhale may be greater than usual (e.g., because of positive airway pressure). Accordingly, some of the pressure may be "vented" during expiration by the patient by increasing the size of vent holes 850 (e.g., to provide greater flow out of the mask). This may allow for easier exhalation by the patient than otherwise. Further, the vent holes may be returned to "normal" in order to facilitate the provision of a better seal during patient inspiration.

Figures 1, 8G:
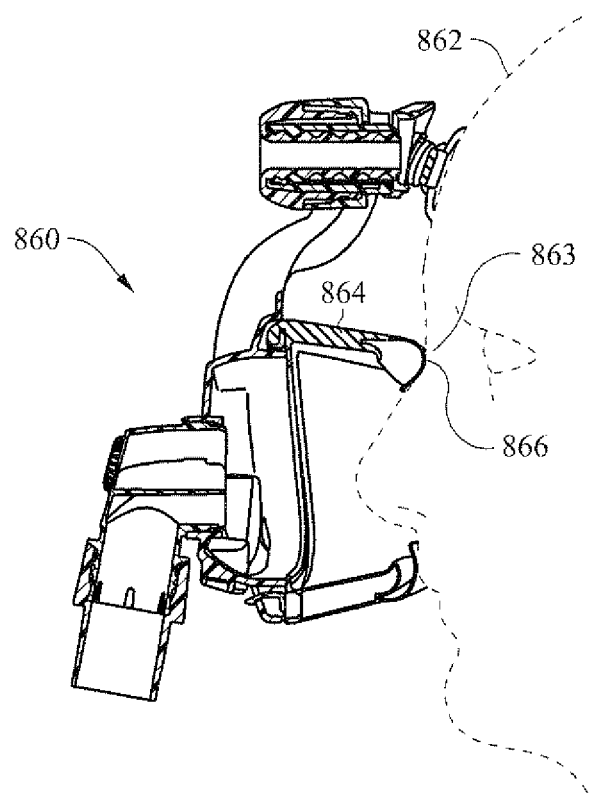
Figures 2, 8G:
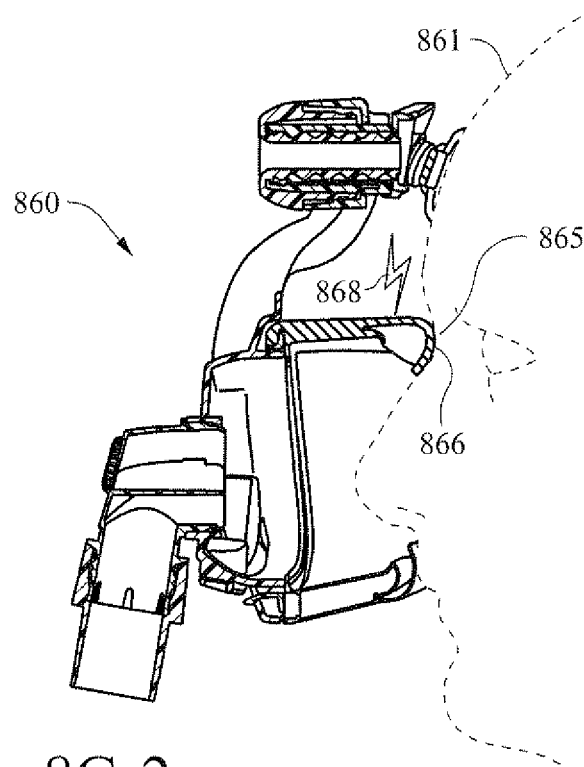

FIGS. 8G-1 and 8G-2 are illustrative cross-sectional views of an example patient interface with an example cushion that is fitted to two different patients with different facial characteristics. Patient facial features may be different from person to person. These different facial features can sometimes increase the difficulty of determining what type of mask or what type of interface is to be used for the patient. In certain example embodiments, the shape changing material may be used to facilitate fitting of cushions, masks, etc., to the face of a patient (e.g., to better fit the anthropometrics of a given patient). Here, patient 862 may have a relative flat nose bridge 863. In contrast, patient 861 may have higher nose bridge 865. A patient interface 860 may include shape changing material 864 such that application of a charge 868 may adjust the material 864 into a position that facilitates providing a seal. The amount of charge may be adjusted based on the anthropometrics of the patient. Thus, in FIG. 8G-1, a charge may not be applied to material 864 due to the relatively flat nose bridge of patient 862. However, in FIG. 8G-2 a charge 868 may be applied so that material 866 better contacts with the nose bridge region of the patient 861 (e.g., due to the high nose bridge of patient 861).

In certain example embodiments, a patient interface may include one or more sensors within a cushion. The sensors may operate to determine how much charge should be applied to a given area of a patient's face in order to facilitate an improved fit of the cushion to the patient's face. For example, one sensor may be disposed in/on the cushion at a position where cushion typically contacts the nose bridge of the patient. Based on readings from the sensor, a charge may be applied to that nose bridge area of the cushion such that the cushion changes shape to properly interfaces with the nose bridge of the patient (e.g., as shown in FIGS. 8F-1 and 8F-2).

In certain example embodiments, the configuration of how much charge is to be applied to a cushion in order to achieve a proper fit for a given patient may be done with the assistance of a medical professional. For example, when a patient first obtains a mask a fitting session may be done that determines how much or how little charge should be applied to various areas of the face of the patient in order to facilitate the formation of a seal. The obtain information may be stored in a storage unit (e.g., non-volatile memory). This storage location may be located on the mask, a flow generator, or other component of a respiratory assistance system. In certain example embodiments, the memory may interface with such systems (e.g., through a Universal Serial Bus port with the storage information stored on a USB drive). This may allow for portability of the readings.

Figures 1, 8H:
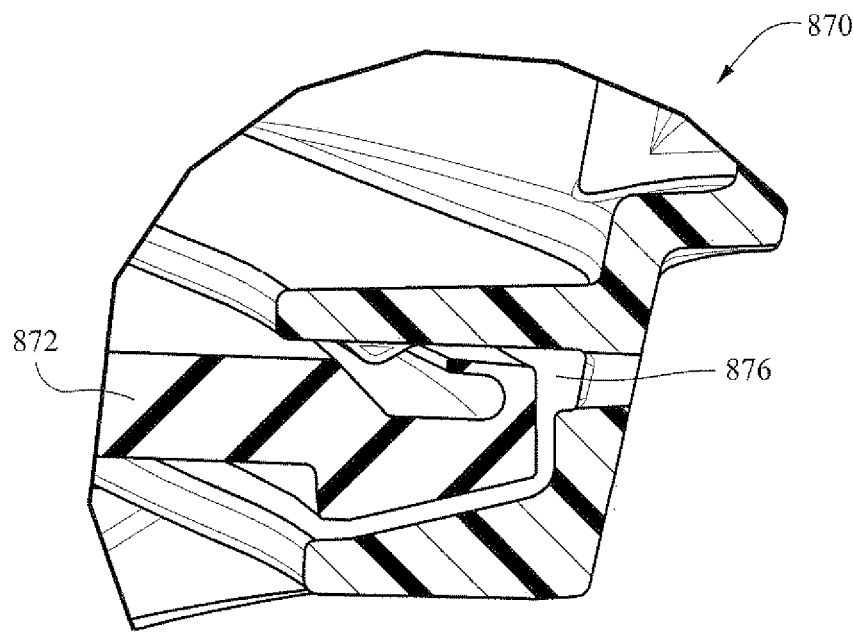
Figures 2, 8H:
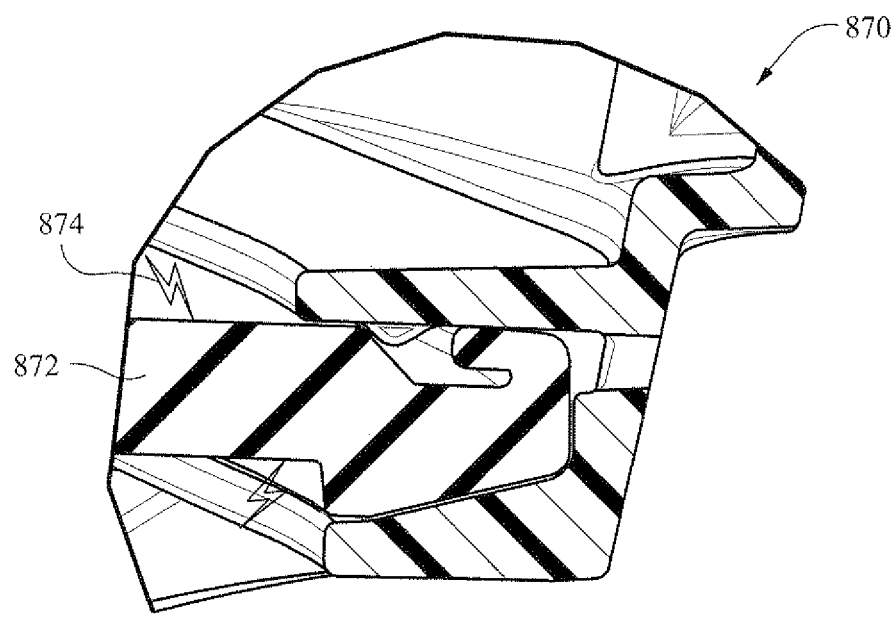

FIGS. 8H-1 and 8H-2 are illustrative cross-sectional views of an example cushion that is integrated into an example frame of a patient interface. Here, a cushion 872 of a patient interface 870 may be supplied in a channel 876 of a frame. The cushion 872 may be loosely fitted into the frame such that the cushion remains secured to the frame even though the cushion is not tightly sealed into the channel 876. This may allow, for example, easier initial placement of the patient interface 870 onto the face of the patient. In FIG. 8H-2, a charge 874 is applied to the shape changing material of the cushion 872. This charge 874 may cause the cushion 872 to expand into the frame channel and thereby cause the cushion to seal with the frame. In certain example embodiments, such a charge may be initially applied when a treatment session starts. For example, if a patient is receiving CPAP therapy the charge may be initiated when a flow generator is turned on.

In certain example embodiments, the charge may be applied when a flow generator attached to a patient interface is turned on. Thus, a patient may place a patient interface into position when the cushion is loosely fitted into the channel (e.g., no charge applied). Once the patient interface is in place, the patient may turn on a flow generator and a charge may be applied to the cushion. The cushion may expand and form a seal with the frame of the patient interface. Similarly, after finishing with the patient interface the charge may be turned off, shrinking the cushion and allowing easier removal of the patient interface from the head of the patient.

Cuff

The shape changing material may be applied to other components of a respiratory assistance system. For example, a tube may connect the patient interface to a flow generator. The tube, or a portion of the tube, may be formed out of the shape changing material. FIGS. 8I-1 and 8I-2 are illustrative cross-sectional views that show an example cuff of a tube interacting with an exemplary elbow. As part of a flow system 880, a cuff portion 882 of a tube may be mated to an elbow portion 886. In certain example embodiments, the elbow may be swively mounted to freely rotate about at least one axis in order to help prevent entangling a hose that connects the flow generator and the patient interface. In FIG. 8I-1 the cuff portion 882 may be in a non-operational state (e.g., the cuff portion may be smaller than the elbow portion 886). In this state, the cuff portion 882 may be smaller in order to facilitate insertion of the cuff portion 882 into the elbow portion 886. In FIG. 8I-2 a charge 884 may be applied to the cuff portion 882 with the shape changing material. The application of the charge may increase the size of the cuff to more firmly interface with the sidewalls of the elbow portion 886 (e.g., lock the cuff in place). This may create a seal and allow for increased airflow efficiency from/to the elbow portion 886 and the cuff portion 882.

In certain example embodiments, the size difference between the cuff portion and the elbow portion may be very small such that, frictional forces related to inserting the cuff may still occur. In certain example embodiments, the size difference between the cuff portion and the elbow portion may be larger such that little or no friction is applied with the cuff is inserted. In certain example embodiments, the charge 884 may be triggered when a flow generator of the flow system 880 is turned on.

Elbow

FIGS. 9A and 9B are illustrative views that show an elbow according to certain example embodiments. FIG. 9C is an illustrative cross-sectional view of FIG. 9B. An elbow 900 of a flow system may be rotatable. For example, the arm portion 902 of the elbow 900 may rotate to position 903A or 903B. The arm portion 902 may rotate with respect to an interface portion 906 (e.g., that is located on a flow generator). Such rotation, in certain instances, of the elbow, or the arm portion thereof, may increase the effects of tube drag from the rotating and/or changing of position. Accordingly, in certain example embodiments, the arm portion and/or the interface portion may be at least partially formed with the shape changing material described herein. Thus, a charge 904 applied to the shape changing material may increase the size of the portion to which it is applied. This increased size of the interface portion 906 or the arm portion 902 may act to increase the frictional resistance between the two portions. In certain example embodiments, the application of the charge 904 to the arm portion 902 or the interface portion 906 may act to "lock" the arm portion 902 at a particular position. In certain example embodiments, this may reduce tube drag. In certain example embodiments, locking the arm portion 902 may provide a more stable platform for the elbow (e.g., such that the arm is not always freely movable.

Sleep Mat

For certain patients, side sleeping may a preferable sleeping position. Such a position may also reduce apnea events.

Figure 10A:
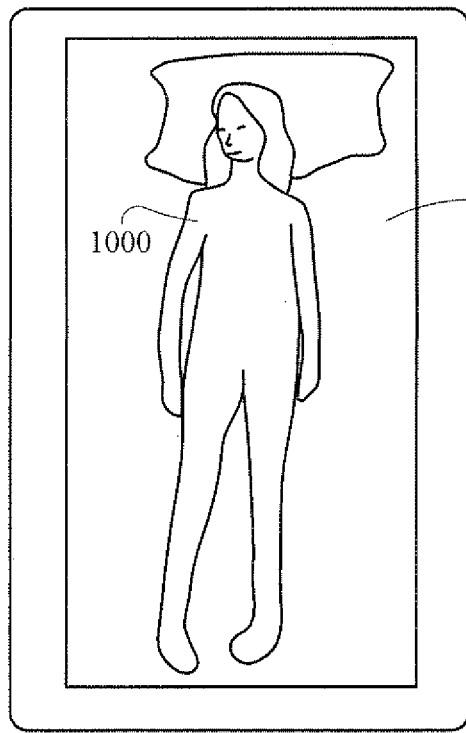
FIGS. 10A and 10B are illustrative views of a patient on an example sleeping mat.
Figure 10B:
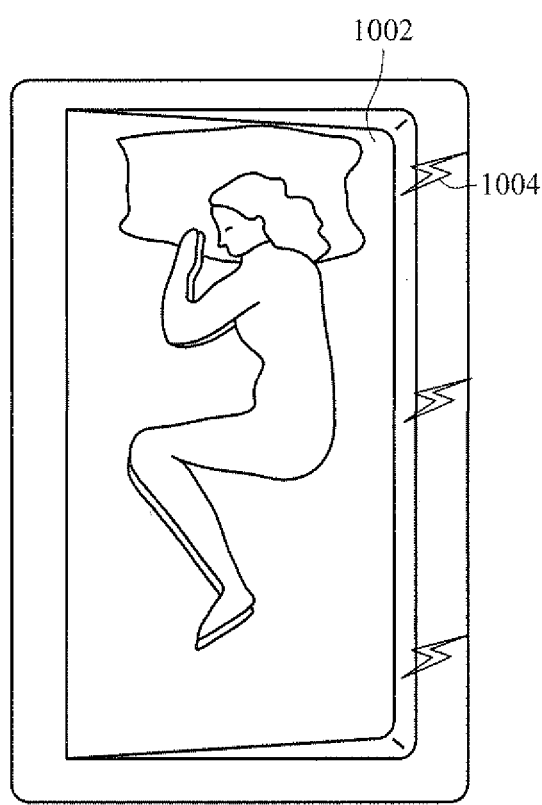
Figure 10C:
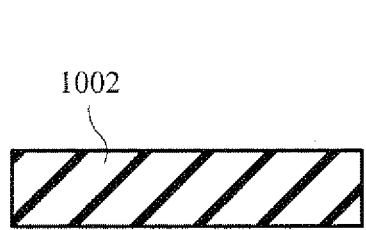
FIGS. 10C-10D are illustrative cross-sectional views of the example sleep mat shown in FIGS. 10A and 10B.
Figure 10D:
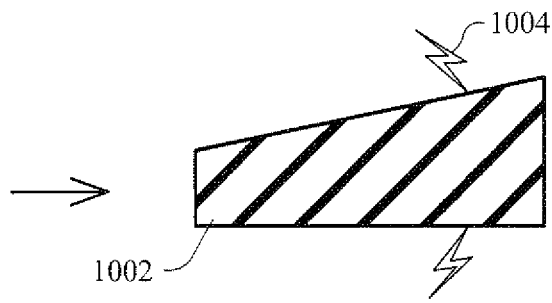

FIGS. 10A and 10B are illustrative views of a patient on a sleeping mat according to certain example embodiments. FIGS. 10C-10D are illustrative cross-sectional views of the example sleep mat shown in FIGS. 10A and 10B. A sleeping mat 1002 may be formed out of the shape changing material. A patient 1000 may be monitored by a sensor or other determination system. The system may monitor whether a patient is sleeping on their back or front (e.g., as shown in FIG. 10A). Based on this determination, the sleeping mat 1002 may have a charge 1004 applied to it. This charge may act on the shape changing material of the mat 1002 and increase the size or the shape of the mat 1002 in a particular region (as shown on the right side of FIG. 10B). This increase in size may act to facilitate (or in some instances even force) the patient 1000 to turn onto their side while sleeping.

In certain example embodiments, the sleep mat may be a sheet or mattress that is used by the patient. In certain example embodiments, a sleep mat may be divided into multiple different sections. For example a sleep mat may have a left section (e.g., left of patient 1000), a center section, and right section (e.g., to the right of patient 1000 in FIG. 10A). The different sections may be adjusted to assist or cause a patient to roll over. In certain example embodiments, the direction that a patient is to roll may be varied based on where a patient is sleeping on the mat. For example, if a patient is sleeping on the left side of the bed, the system may increase the height of the mat on the left side, as opposed to the right side (as shown in FIG. 10B) in order to cause or assist the patient in turning onto their left side.

In certain example embodiments, one or more sensors may be disposed on or in the mat to determine where a patient is sleeping on the sleep mat. For example, a force sensor may be used. The sensors may monitor one or more (e.g., all the sections) to the sections in a sleep mat.

Figure 10E:
FIGS. 10E, 10F, and 10G are illustrative cross-sectional views of an example sleep mat with a charge applied or reduced to one or more portions of the sleep mat.
Figure 10F:
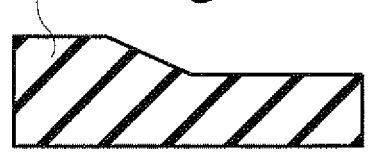
Figure 10G:
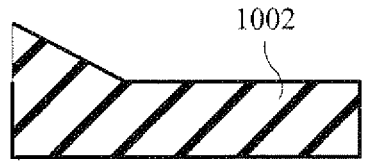

In certain example embodiments, one side of a sleep mat may be reduced instead of increased in order to facilitate the turning of the patient. For example, a mat may be supplied at a default size. Application (or removal) of a charge to a portion of the sleep mat may decrease the size (e.g., thickness) of the mat in that area. In certain example embodiments, a sleep mat may be divided into multiple different portions that each may be increased and/or reduced in size. Accordingly, in certain example embodiments, a sleep mat may be adjusted such that different cross sections may be formed as a result of varying the thickness of the sleep mat. For example, cross sections as shown in FIGS. 10E, 10F, and 10G may be formed by applying a charge to one or more portions of the sleep mat and/or reducing or removing a charge from one or more sections of the sleep mat.

In certain example embodiments, the top (or bottom) of the sleep mat may be linear (e.g., as shown in FIG. 10D). In certain example embodiments the top (or bottom) may be non-linear. For example, a cross-section may be a half-oval (or circle). In certain example, the oval (or other shape) may be concave or convex.

In certain examples, a sleep mat may function to cause a patient to roll to an outward edge of the sleep mat (e.g., if the patient is at the center of the sleep mat). In certain example, the sleep mat may function to cause a patient to roll towards a more inner location on the sleep mat (e.g., if the patient is at the edge of the sleep mat).

Flow Generator

Figure 11A:
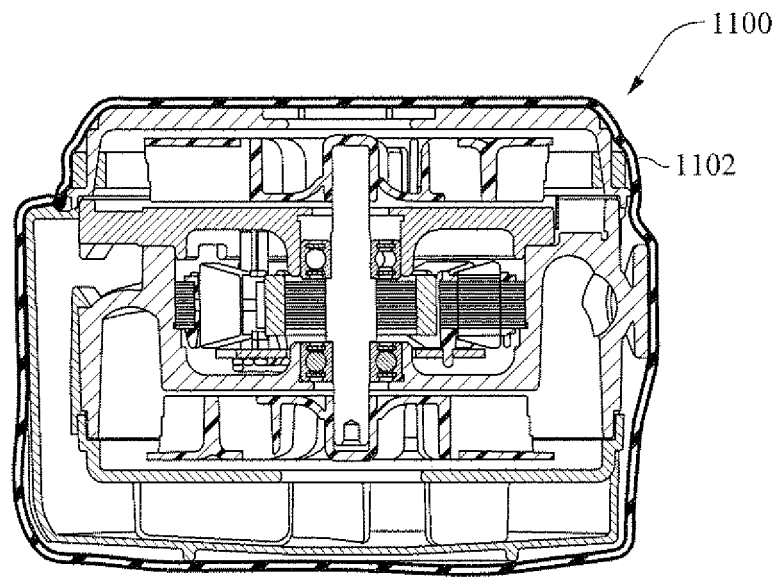
FIGS. 11A and 11B are illustrative cross-sectional views that show an example flow generator with exemplary noise dampening according to certain example embodiments.
Figure 11B:
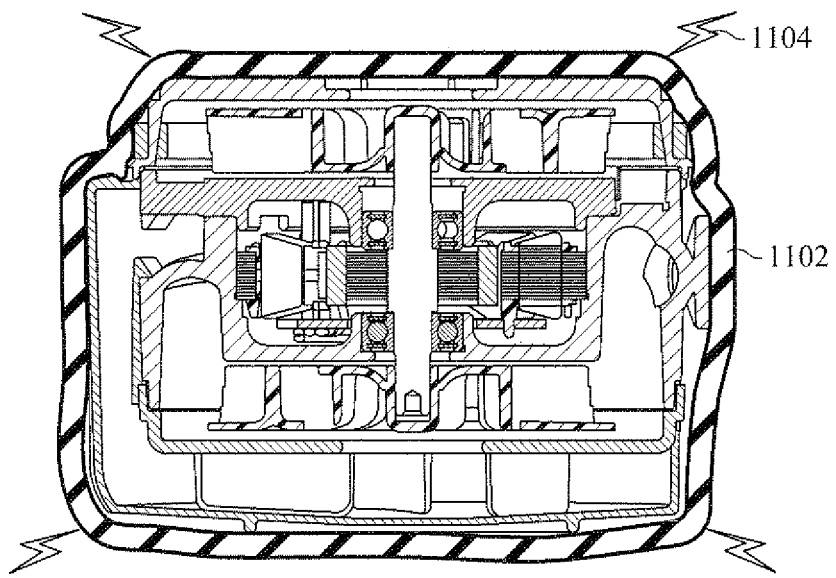

FIGS. 11A and 11B are illustrative cross-sectional views that show an example flow generator with exemplary noise dampening shell made of electro active polymer. In certain instances, when a flow generator 1100 runs at a higher RPM, the noise produced by the flow generator can increase. Accordingly, certain example embodiments may include a housing 1102 that is formed at least in part of the shape changing material. The housing may encompass the flow generator and/or components thereof. When the flow generator increases RPM, a charge 1104 may be sent to the housing and cause the housing 1102 to increase in size. In certain example embodiments, a trigger to send a charge may be based on a detected sound level (e.g., from a microphone or other sensor). In certain example embodiments, application of a charge may be tied to the above mentioned RPM of the flow generator. In certain example embodiments, the quantity of charge provided to the housing may vary depending on the detected parameter. For example, a sound level of 5 may correspond to a charge of 5. Similarly, a sound level of 10 may correspond to a charge of 10. Thus, the sound absorption capability may vary. In certain example embodiments, there may be two states of charge, on and off.

Splint

FIGS. 12A and 12B are illustrative cross-sectional views of an example splint. A splint 1200 may be used as a throat splint and may be formed out of the shape changing material. In certain example embodiments, a charge 1202 may be applied to the splint 1200 such that the splint expands to force an airway of the patient open and/or prevent the airway from collapsing. A sensor may be provided to determine when a charge may be applied to prevent collapse of a patient's airway.

Peristaltic Pump

The shape changing material may also be applied to form a peristaltic pump. FIG. 13A is an illustrative cross-sectional view of an example pump according to certain example embodiments. Pump 1300 includes a series of regions 1302A, 1302B, and 1302C that may act to form a pumping action by opening and closing gates 1304, 1306, and 1308. Specifically, the gates may be formed with the shape changing material such that when a charge 1310 is applied to one of the gates the gate being charged opens to allow airflow 1303 from one region to another region. In certain example embodiments, the pump may be part of a tube system that connects, for example, a flow generator to a patient interface. In certain example embodiments, the pump may be a different portion that supplements or attaches to the tube or another component of a respiratory assistance system.

In certain example embodiments, the pump may include a balloon made of the shape changing material and may be attached to a tube containing a series of valves. The balloon may be periodically charged to create a pumping action. Gas that is sent from the balloon may then be sent down the tube with the valves being periodically charged causing them to open and close. In certain example embodiments, the opening and closing of the valves may be used to tune the pressure being delivered to a patient.

Figures 1, 13B:
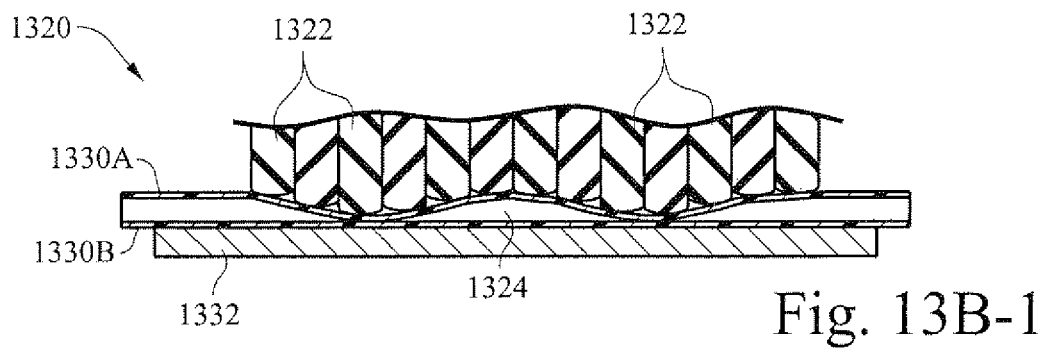
Figures 2, 13B:
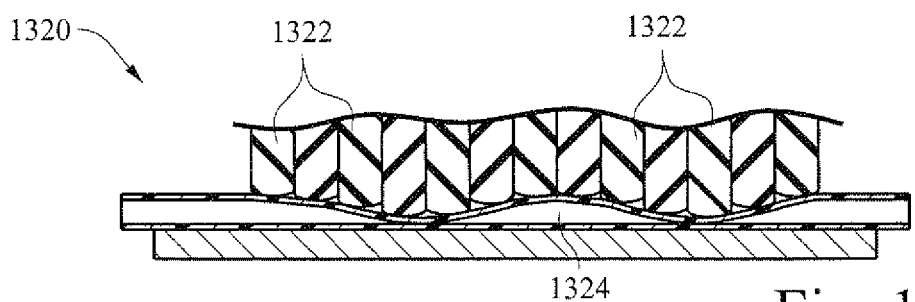
Figures 3, 13B:
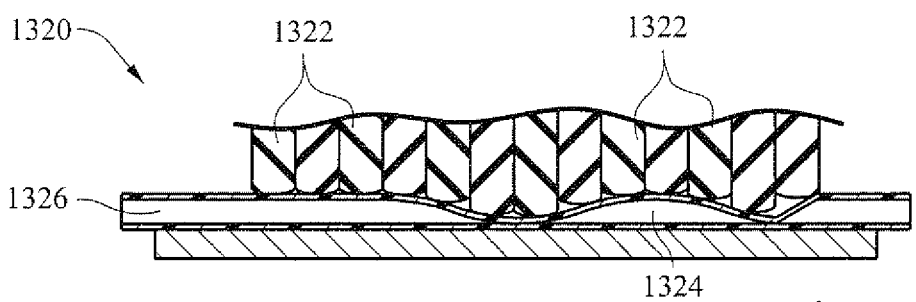
Figures 4, 13B:
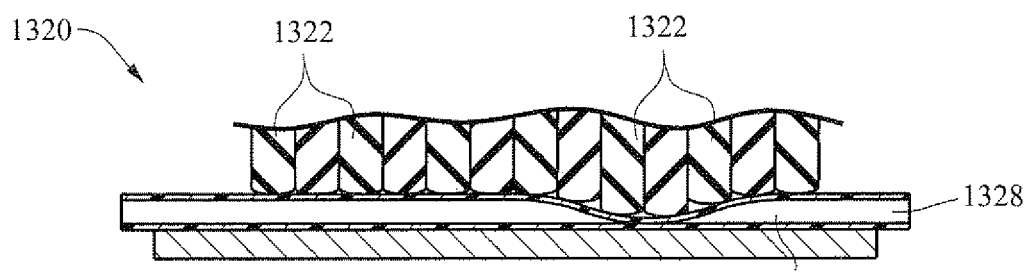

FIGS. 13B-1-13B-4 are illustrative cross-sectional views of another example pump according to certain example embodiments. A pump 1320 may include multiple fingers 1322 that are formed out of the shape changing material. The fingers may be disposed against a flexible material 1330A. Opposing the fingers 1322 and the flexible material 1330A may be a solid base portion 1332 that is disposed against another flexible material 1330B. In operation, charges may be applied to the fingers 1322 such that each of the fingers may vary in height with the corresponding charge. The variance in height may create a pocket 1324 between the two flexible materials 1330A and 1330B. The charge applied to the fingers may be adjusted such that the pocket 1324 "moves" from the airflow delivery end 1326 (e.g., the flow generator end) to the airflow receiving end 1328 in FIG. 13B-4. Accordingly, a pumping action for pressurized breathable gas may be performed.

Figure 14:
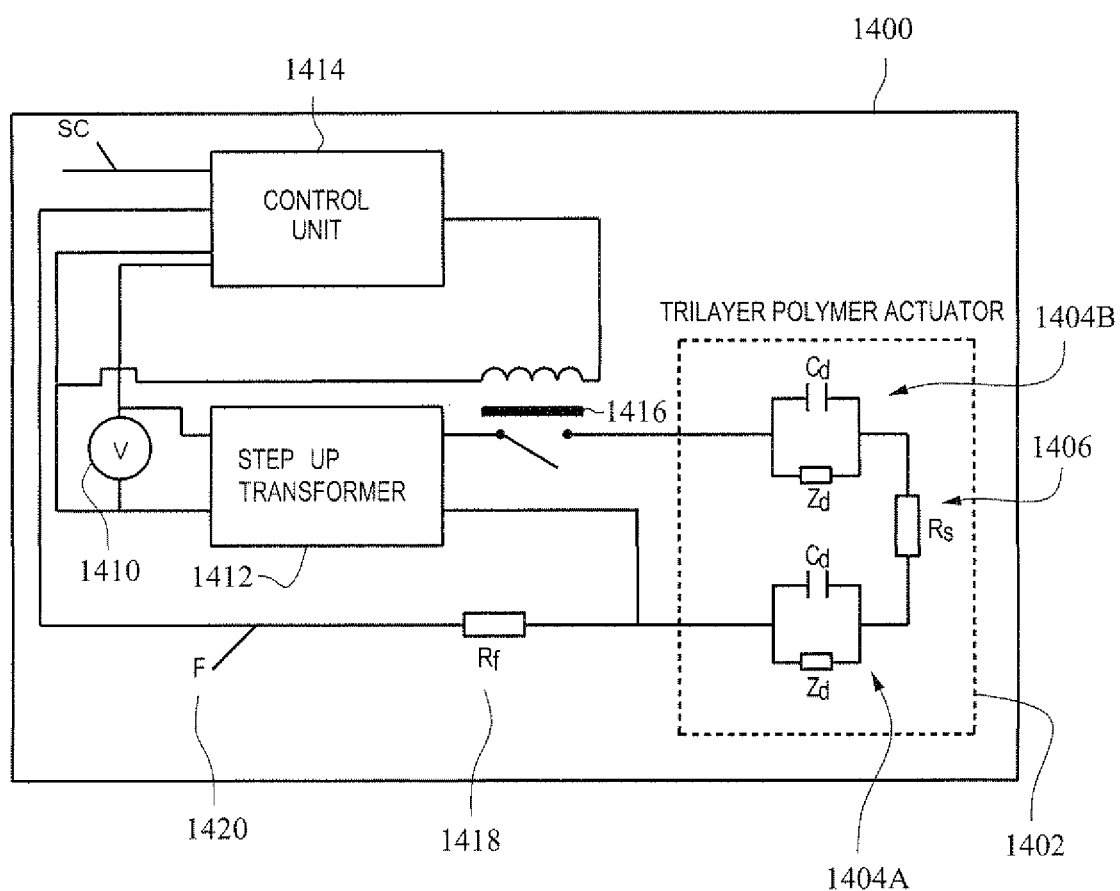
FIG. 14 illustrates an example electrical circuit configured to supply power to an example electro-polymer according to certain example embodiments.

FIG. 14 illustrates an example electrical circuit configured to supply power to an example electro-polymer according to certain example embodiments. An electrical circuit 1400 is provided for controlling a dielectric electro active polymer actuator 1402, such as the polymer actuators of FIG. 1D or FIG. 4C. A conceptual diagram of the actuator is shown at 1402. The actuator may include a polymer layer 1406 sandwiched between two electrodes 1404A and 1404B. The electrodes are shown with an associated capacitance C and impedance Z. The polymer layer 1406 is shown with an associated resistance Rs. It will be appreciated that other embodiments may include a different number of layers (e.g., 1, 2, or 3).

For the example electrical circuit 1400, A DC voltage V 1410 is supplied either from a flow generator or from an external power source. In certain example embodiments, the supplied voltage would be in the order of 12 Volts or 24 Volts. However, it will be appreciated that other voltage values may be used (e.g., less than, more than, or in between). A voltage step up module 1412 may be provided to supply an increased voltage to the polymer. For example, in certain instances, the voltage may be stepped up to one kilovolt or more. It will be appreciated that this voltage may vary depending on the particular system the actuator is implemented in. The power supply also provides power to a control unit 1414, which functions to control a relay 1416. The use of relay 1416 allows the high voltage provided to the polymer to be switched on and off by way of a low voltage control signal from the control unit 1414.

The control unit 1414 may be arranged to control the charging level (the provided voltage or current) in a stepwise manner, thus causing a substantially stepwise change in the shape and/or the size of the polymer portion. This may include a single step, or a plurality of smaller steps. Alternatively, the voltage or current may be increased (or decreased) in a continuous manner, thus imparting a gradual change in the shape and/or size of the controlled polymer. A combination between the two methods may also be applied.

A force that acts on the polymer may cause deflection of the polymer and change the electrical impedance associated with the polymer actuator. In certain instances, This allows in certain embodiments the polymer actuator to be used for sensing at least one parameter associated with providing of a breathing assistance to the patient based on such deflection or electrical impedance. In this configuration, a measured change of at least one electrical characteristic of the polymer of the flap provides an indication of an associated change in the at least one parameter. In certain example embodiments, measurement of the change in the impedance may be used to obtain information of the pressure applied to the flap or other respiratory component using the polymer. This provides information of the airflow (e.g. in the vent 400) or of the patient's breathing. In certain example embodiments, the electrical impedance may also indicate the position of the flap (or other structure). For example, the flap may be under different pressures depending on the position it has adopted. Accordingly, in certain example embodiments an optional feedback line 'F' 1420 may be included to provide a signal from the actuator to the control unit. A resistor 'RF' 1418 may also be used to drop a high voltage back to a level that is acceptable to the control unit.

In certain example embodiments, when the polymer is bent and a flap is in a closed position (e.g., as shown in FIG. 4C), the feedback line F may be used in the electrical circuit 1400 to sense the therapy pressure at the patient end of the flow generator circuit. In other words, an increase in total electric impedance of the polymer actuator changes the voltage and the current across the resistor 1418. By sensing this current or voltage change across the resistor 1418 and using a predetermined relationship between such a change and a corresponding change in the therapy pressure, the therapy pressure may be estimated. Such an implementation may also be used when the polymer is in the open position of FIG. 4A to detect changes in pressure due to the user breathing.

In certain example embodiments, the resistor 1418 may be configured to provide heated air to a tube (e.g., to increase patient comfort). In certain example embodiments, a secondary controller SC (not shown) can provide an input to the main polymer control unit 1414. The secondary controller may take inputs from a flow generator (not shown), such as pressure signals or flow signals or temperature signals or other signals and use this information to determine when to activate the polymer (e.g., from the respective positions shown in FIG. 4C). For example, if the secondary controller determines that the therapy pressure is too low to provide adequate vent flow in a vented system, the polymer may be adjusted via electro stimulation to various positions (e.g., as shown in FIG. 4C) to allow the user increased (e.g., adequate) ventilation. Alternatively, a secondary controller may be used to control the input voltage to a step up voltage circuit so as to allow a continuous control of the position of the polymer or the shape on the polymer. It will be appreciated that the circuit shown in FIG. 14 may be configured to work with various other embodiments discussed herein.

In certain example embodiments, a shape changing material in a component of a respiratory assistance system may change shape in: 1) length; 2) width; or 3) depth/height. In other words, the change in shape may be one dimensional, two dimensional, or three dimensional depending upon a particular application. In certain instances the cross-sectional area of the material may increase or decrease in area.

While the disclosed technology has been described in connection with what are presently considered to be the most practical and preferred embodiments, it is to be understood that the technology is not to be limited to the disclosed embodiments, but on the contrary, is intended to cover various modifications and equivalent arrangements included within the spirit and scope of the technology. Further, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface configured to receive a supply of breathable gas delivered from a continuous positive airway pressure system, the patient interface comprising:

a cushion configured to provide a seal to a region of the face of a patient that surrounds an entrance to the airway(s) of the patient, the cushion including an electro active polymer that changes shape and/or size between at least a first state when no electrical current or voltage is applied to the electro active polymer and a second state when current or voltage is applied to the electro active polymer, wherein the electro active polymer is configured to be selectively energized by a power source that is controlled by a controller, wherein a change between the first state and the second state of the electro active polymer, or vice versa, changes the shape and/or the size in at least one dimension of the cushion.

2. The patient interface of claim 1, wherein different portions of the electro active polymer of the cushion are independently and selectively changeable between the first state and the second state.

3. The patient interface of claim 2, wherein each of the different portions is changeable between the first state and the second state based on a level of charge that is supplied to the respective portion being controlled by the controller.

4. The patient interface of claim 2, wherein the different portions are configured to be charged in an order.

5. The patient interface of claim 4, wherein the order is substantially random or pseudo-random.

6. The patient interface of claim 4, wherein the order is based on at least one criterion.

7. The patient interface of claim 1, wherein the electrical voltage or current is applied to the electro active polymer as a function of a determined state of a respiratory cycle of the patient.

8. The patient interface of claim 1, wherein the electro active polymer of the cushion is divided into a plurality of regions that are each independently and selectively changeable between the first state and the second state.

9. The patient interface of claim 1, wherein the electrical voltage or current applied to the electro active polymer is a function of a determined state of a respiratory cycle of the patient.

10. The patient interface of claim 1, further comprising: at least one transducer that is included within the cushion.

11. The patient interface of claim 10, wherein each of a plurality of regions of the cushion includes a corresponding transducer within the cushion.

12. The patient interface of claim 10, wherein the transducer is at least one of a microphone and a pressure sensor.

13. The patient interface of claim 1, wherein the first state is configured to be applied during exhalation by the patient and the second state is configured to be applied during inhalation by the patient.

14. The patient interface of claim 1, wherein the electrical active polymer is configured to accept different amounts of electrical charge based on anthropometrics of the face of the patient.

15. The patient interface of claim 1, further comprising: a frame that includes at least one channel in which the cushion is disposed.

16. The patient interface of claim 15, wherein the second state of the electro active polymer is configured to cause the cushion to seal with the frame.

17. A continuous positive airway pressure (CPAP) system comprising:
the patient interface of claim 1;
a flow generator that is configured to supply a flow of breathable gas;
the controller to control when electrical current or voltage is applied to the electro active polymer; and
at least one conduit that is configured to deliver the flow of breathable gas from the flow generator to the patient interface.

18. A method of providing a pressurized flow of breathable air to a patient, the method comprising:
securing a patient interface to the face of the patient around an entrance to at least one airway of the patient, the patient interface including a cushion configured to provide a seal to a region of the face of a patient that surrounds an entrance to the at least one airway of the patient, the cushion including an electro active polymer that changes shape and/or size between at least a first state when no electrical current or voltage is applied to the electro active polymer and a second state when current or voltage is applied to the electro active polymer;
providing, to the at least one airway of the patient and via the secured patient interface, the pressurized flow of breathable air; and
while the pressurized flow of breathable air is being provided, applying an electrical charge to the electro active polymer to change the cushion in size or shape while the patient interface is engaged with the face of the patient.

19. The method of claim 18, further comprising:
monitoring at least one parameter associated with the pressurized flow of breathable air that is provided to the patient;
detecting a leak; and
based on detection of the leak, applying the electrical charge to the electro active polymer.

20. The method of claim 18, further comprising:
performing a determination for a respiratory cycle of the patient; and
based on the determination, applying the electrical charge to the electro active polymer.

* * * * *